United States Patent
Gordon et al.

(10) Patent No.: US 9,611,496 B2
(45) Date of Patent: Apr. 4, 2017

(54) PROCESSES FOR EXTRACTING CARBOHYDRATES FROM BIOMASS AND CONVERTING THE CARBOHYDRATES INTO BIOFUELS

(71) Applicant: Cavitation Technologies, Inc., Chatsworth, CA (US)

(72) Inventors: Roman Gordon, Studio City, CA (US); Igor Gorodnitsky, Marina del Rey, CA (US); Vijayanand Suryakant Moholkar, Guwahati (IN)

(73) Assignee: Cavitation Technologies, Inc., Chatsworth, CA (US)

( * ) Notice: Subject to any disclaimer, the term of this patent is extended or adjusted under 35 U.S.C. 154(b) by 492 days.

(21) Appl. No.: 14/100,562

(22) Filed: Dec. 9, 2013

(65) Prior Publication Data
US 2014/0099687 A1    Apr. 10, 2014

Related U.S. Application Data

(63) Continuation-in-part of application No. 12/484,981, filed on Jun. 15, 2009, now Pat. No. 8,911,808, and a continuation-in-part of application No. 12/821,000, filed on Jun. 22, 2010, now Pat. No. 8,603,198.

(51) Int. Cl.
| | |
|---|---|
| *C12P 19/14* | (2006.01) |
| *C12P 7/04* | (2006.01) |
| *C12P 19/02* | (2006.01) |
| *B01F 5/06* | (2006.01) |
| *B01J 10/00* | (2006.01) |
| *B01J 19/00* | (2006.01) |
| *B01J 19/02* | (2006.01) |
| *B01J 19/24* | (2006.01) |
| *B01F 13/10* | (2006.01) |
| *C11B 3/00* | (2006.01) |
| *C11B 3/04* | (2006.01) |
| *C11B 3/16* | (2006.01) |
| *C11C 3/00* | (2006.01) |
| *C10L 1/02* | (2006.01) |
| *C12M 1/02* | (2006.01) |
| *C12M 1/00* | (2006.01) |
| *A23K 10/37* | (2016.01) |
| *A23K 50/10* | (2016.01) |

(52) U.S. Cl.
CPC ............. *C12P 19/14* (2013.01); *A23K 10/37* (2016.05); *A23K 50/10* (2016.05); *B01F 5/0644* (2013.01); *B01F 5/0646* (2013.01); *B01F 5/0652* (2013.01); *B01F 5/0653* (2013.01); *B01F 5/0682* (2013.01); *B01F 5/0688* (2013.01); *B01F 13/1025* (2013.01); *B01F 13/1027* (2013.01); *B01J 10/002* (2013.01); *B01J 19/008* (2013.01); *B01J 19/0066* (2013.01); *B01J 19/02* (2013.01); *B01J 19/2415* (2013.01); *C10L 1/023* (2013.01); *C11B 3/001* (2013.01); *C11B 3/006* (2013.01); *C11B 3/04* (2013.01); *C11B 3/16* (2013.01); *C11C 3/003* (2013.01); *C12M 27/00* (2013.01); *C12M 45/06* (2013.01); *C12P 7/04* (2013.01); *C12P 19/02* (2013.01); *B01J 2219/0218* (2013.01); *B01J 2219/0231* (2013.01); *B01J 2219/0245* (2013.01); *Y02P 60/877* (2015.11)

(58) Field of Classification Search
CPC ...................................................... C12P 19/14
See application file for complete search history.

(56) References Cited

U.S. PATENT DOCUMENTS

| | | |
|---|---|---|
| 1,454,196 A | 5/1923 | Trood |
| 1,626,487 A | 4/1927 | Warren |
| 3,167,305 A | 1/1965 | Backx et al. |
| 4,014,961 A | 3/1977 | Popov |
| 4,213,712 A | 7/1980 | Aanonsen |
| 4,280,962 A | 7/1981 | Watanabe et al. |
| 4,698,185 A | 10/1987 | Dijkstra et al. |

(Continued)

FOREIGN PATENT DOCUMENTS

| | | |
|---|---|---|
| DE | 10310442 A1 | 9/2004 |
| GM | 77 33 456 U1 | 5/1978 |

(Continued)

OTHER PUBLICATIONS

Branson Ultrasonic Corporation; Ultrasonic Liquid Processing; Technical specification on Branson's ultrasonic liquid processing cell; USA; Sep. 1986.

(Continued)

*Primary Examiner* — Randy Boyer
(74) *Attorney, Agent, or Firm* — Kelly & Kelley, LLP

(57) ABSTRACT

A process for extracting carbohydrates from biomass and creating bioalcohol from the extracted carbohydrates. Subjecting the biomass to acid or alkali hydrolysis in a first hydrodynamic cavitation process. Filtering the first cavitated biomass to separate a first filtrate containing extracted carbohydrates. Fermenting the first filtrate to create a bioalcohol and separating the bioalcohol by distillation or similar process. Subjecting the biomass to enzymatic hydrolysis in a second hydrodynamic cavitation process. Filtering the second cavitated biomass to separate a second filtrate containing extracted carbohydrates. Fermenting the second filtrate to create a bioalcohol and separating the bioalcohol by distillation or similar process. The first and second filtrates may be combined and fermented in a single step.

6 Claims, 14 Drawing Sheets

(56) References Cited

U.S. PATENT DOCUMENTS

| | | | |
|---|---|---|---|
| 4,698,186 | A | 10/1987 | Jeromin et al. |
| 5,302,325 | A | 4/1994 | Cheng |
| 5,492,654 | A | 2/1996 | Kozjuk et al. |
| 5,514,820 | A | 5/1996 | Assmann et al. |
| 5,696,278 | A | 12/1997 | Segers |
| 5,849,939 | A | 12/1998 | Mittelbach et al. |
| 5,937,906 | A | 8/1999 | Kozyuk |
| 5,969,207 | A | 10/1999 | Kozyuk |
| 5,971,601 | A | 10/1999 | Kozyuk |
| 6,200,486 | B1 | 3/2001 | Chahine et al. |
| 6,227,694 | B1 | 5/2001 | Mitake et al. |
| 6,276,823 | B1 | 8/2001 | King |
| 6,279,653 | B1 | 8/2001 | Wegener et al. |
| 6,440,057 | B1 | 8/2002 | Ergun et al. |
| 6,489,496 | B2 | 12/2002 | Barnhorst et al. |
| 6,502,979 | B1 | 1/2003 | Kozyuk |
| 6,705,396 | B1 | 3/2004 | Ivannikov et al. |
| 6,935,770 | B2 | 8/2005 | Schueler |
| 6,955,753 | B1 | 10/2005 | Gomez |
| 6,979,757 | B2 | 12/2005 | Powers |
| 7,086,777 | B2 | 8/2006 | Kozyuk |
| 7,135,155 | B1 | 11/2006 | Long, Jr. et al. |
| 7,207,712 | B2 | 4/2007 | Kozyuk |
| 7,247,244 | B2 | 7/2007 | Kozyuk |
| 7,247,739 | B2 | 7/2007 | Gapes et al. |
| 7,338,551 | B2 | 3/2008 | Kozyuk |
| 8,143,460 | B2 | 3/2012 | Kozyuk |
| 8,430,968 | B2 | 4/2013 | Mancosky et al. |
| 2005/0027137 | A1 | 2/2005 | Hooker |
| 2005/0237855 | A1 | 10/2005 | Kozyuk |
| 2006/0063242 | A1 | 3/2006 | Chou |
| 2006/0224005 | A1 | 10/2006 | Felly |
| 2007/0041266 | A1 | 2/2007 | Huymann |
| 2007/0055073 | A1 | 3/2007 | McGurk |
| 2007/0189114 | A1 | 8/2007 | Reiner et al. |
| 2008/0044891 | A1* | 2/2008 | Kinley ............... C12M 21/12 435/289.1 |
| 2009/0038210 | A1 | 2/2009 | Kozyuk et al. |
| 2009/0043118 | A1 | 2/2009 | Kozyuk |
| 2009/0141585 | A1 | 6/2009 | Al-Otaibi |
| 2009/0186383 | A1* | 7/2009 | Mancosky ............ C07H 1/06 435/72 |
| 2010/0012583 | A1* | 1/2010 | Stuart .................. C12P 7/06 210/633 |

FOREIGN PATENT DOCUMENTS

| | | |
|---|---|---|
| JP | 62-221426 A2 | 9/1987 |
| LV | 12900 B | 2/2003 |
| RU | 1790438 A3 | 1/1993 |
| SU | 633576 | 11/1978 |

OTHER PUBLICATIONS

Branson Ultrasonic Corporation; Technical drawing sheet, 1" Dia. Hi Pressure Proc. Cell Assy, Dwg. No. 101-123-007; Dec. 1978.
Branson Ultrasonic Corporation; Technical drawing sheet, Orifice Plug—1" Dia Hom, Dwg. No. 100-080-064; Jul. 28, 1978.
Moulton KJ, Wang Lc; A Pilot-Plant Study of Continuous Ultrasonic Extraction of Soybean Protein (1982); J. Food Sci. 47: 1127-1129.
Moulton KJ, Koritala S, Warner K, Frankel En; Continuous Ultrasonic Hydrogenation of Soybean Oil. II. Operating Conditions and Oil Quality (1987); J. Am. Oil Chem. Soc. 64: 542-547.
Moulton KJ; Processing with ultrasonic energy (1989); J. Am. Oil Chem. Soc. 66: 896-904.
Moulton KJ, Koritala S, Frankel EN; Ultrasonic hydrogenation of soybean oil; (1983) J. Am. Oil Chem. Soc. 60: 1257-1258.
Sinram RD; Nephelometric determination of Phosphorus in Soybean and Corn-oil Processing (1986); J. Am. Oil Chem. Soc. 63: 661-610.
Snyder J, Mounts T, Holloway R; An Analysis Scheme for Estimation of Crude Oil Quality (1991); J. Am. Oil Chem. Soc. 68: 285-288.
Liu H, Przybylski R, Eskin Nam; Turbidimetric Measurement of Haze in Canola Oil by Acetone Precipitation (1996); J. Am. Oil Chem. Soc. 73: 1557-1560.
K. Mahesh, G. Constantinescu, P Moin; A numerical method for large-eddy simulation in complex geometries; Journal of Computational Physics; Nov. 19, 2003; pp. 215-240; vol. 197; Elsevier Inc.
Xiangbin Li, Guoyu Wang, Mindi Zhang, Wei Shyy; Structures of supercavitating multiphase flows; International Journal of Therman Sciences; Nov. 24, 2001; pp. 1263-1275; vol. 41; Elsevier Masson SAS.
FlowMaxx Engineering, Cavitating Venturis, web article, 1 page, www.flowmaxx.com/cavitate.htm, Mar. 2010 USA.
FlowMaxx Engineering, Venturi Flowmeters, web article, 5 pages, www.flowmaxx.com/cavitate.htm, Mar. 2010 USA.
Gogate, P. et al., A review and assessment of hydrodynamic cavitation as a technology for the future, 2005, Ultrasonics Sonochemistry, 12, pp. 21-27.
Kelkar, M.A. et al., Intesificatin of esterification of acids for synthesis of biodiesel using acoustic and hydrodynamic cavitation, Jan. 4, 2008, Ultraxonics Sonochemistry, 15, pp. 188-194.
Li, S. et al., Static Mixers, 2002, Fluent News, vol. XI, Issue 1, pp. cover, & 12.
Gogate, Parag R. et al., Cavitation: A technology on the horizon, Jul. 10, 2006, Current Science, vol. 91, No. 1.

* cited by examiner

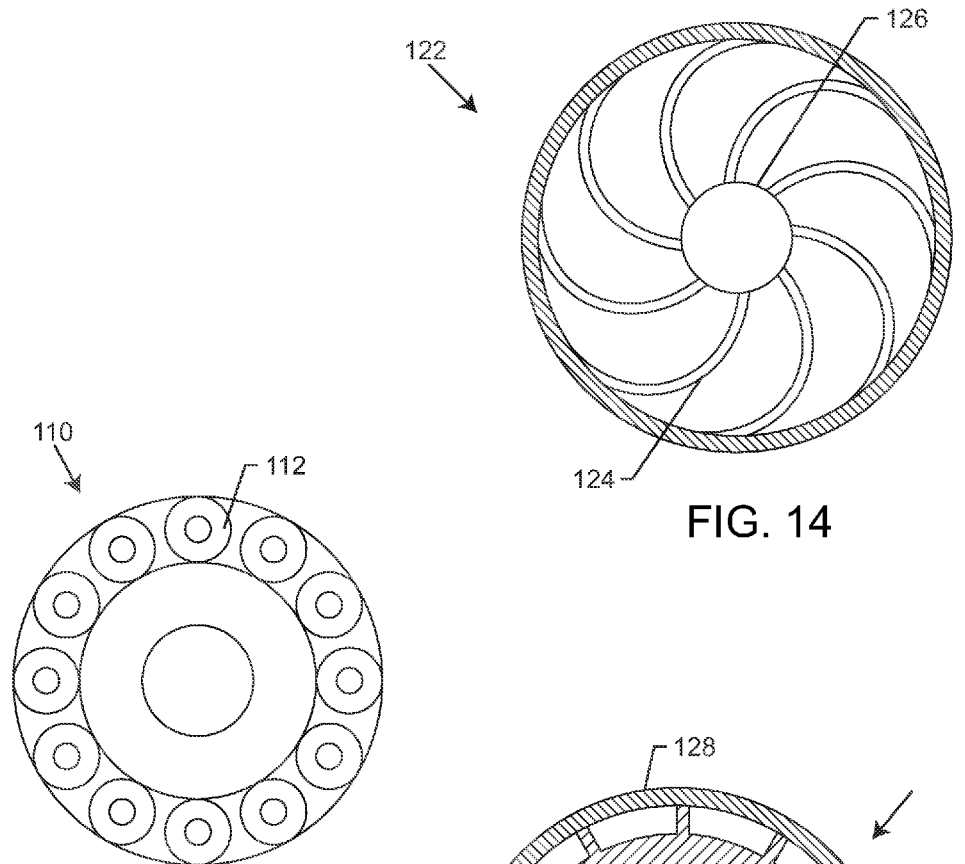
FIG. 14
FIG. 15
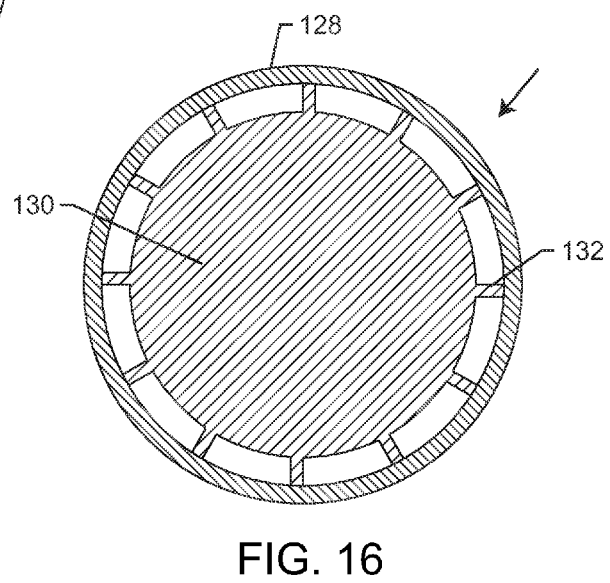
FIG. 16

PROCESSES FOR EXTRACTING CARBOHYDRATES FROM BIOMASS AND CONVERTING THE CARBOHYDRATES INTO BIOFUELS

FIELD OF THE INVENTION

The present invention is directed to a multi-step process for producing biofuels, in particular bioalcohol, using hydrodynamic cavitation. More particularly, the present invention is directed to: (1) a process for the extraction of carbohydrates from biomass using hydrodynamic cavitation; and (2) a process for converting the carbohydrates into bioalcohol using hydrodynamic cavitation.

The present invention uses hydrodynamic cavitation for processing heterogeneous and homogeneous liquid systems via a static mechanical device that creates cavitation in a fluidic flow. The cavitation facilitates synthesis of intermediate and final products in the overall production of biofuels. The method may also find application in other areas of fluid processing and other fields of industry.

BACKGROUND OF THE INVENTION

Alcoholic biofuels (or bioalcohol), such as methanol, ethanol, butanol, propanol, etc., may be derived from biological materials, i.e., biomass. Such production can proceeding by typical chemical processing, as is used with natural gas, or by fermentation of sugars. Prior art bioalcohols may be derived from a number of sources, many of which are time consuming and/or cost intensive to produce or manufacture. The prior art processes for producing bioalcohols would benefit greatly from an improved and more efficient method of producing alcohol.

Existing technologies in processing industries are similar in concept in that they all require an input of energy to produce a final product. For example, some technologies include a pressurized homogenizer, which uses a sequential valve assembly to increase fluid pressure in the material being processed. Such a device requires a large energy input, producing a high outlet pressure, usually in excess of 5,000 psi.

Cavitation is defined as the generation, subsequent growth and ultimate collapse of vapor- or gas-filled cavities in liquids resulting in significant energy release. As understood in this broad sense, cavitation includes the familiar phenomenon of bubble formation when water is brought to a boil under constant pressure. In engineering and science, the term cavitation is used to describe the formation of vapor-filled cavities in the interior or on the solid boundaries created by a localized pressure reduction produced by the dynamic action of a liquid system.

Hydrodynamic cavitation is essentially generated by a change in bulk pressure in a liquid flow by variation of the velocity of the flow through well-defined geometries. In the simplest situation, hydrodynamic cavitation can be generated by forcing or throttling high pressure discharge from a pump through constrictions such as a venturi or an orifice. In this case, the velocity of the flow increases with reducing flow area causing a concurrent reduction in bulk pressure. If the throttling is sufficient, the pressure in the flow in the region downstream of the constriction may actually fall to or even below the vapor pressure of the medium. This causes the release of dissolved gas in the medium or generation of vapor bubbles in the liquid medium. These bubbles undergo oscillation with a recovery of pressure in the region further downstream resulting in a final transient collapse. The oscillations of the bubbles generate intense microturbulence in the medium causing vigorous mixing.

For a heterogeneous reaction system, this turbulence can create a fine emulsion between phases generating high interfacial area that can enhance the reaction kinetics. At the transient collapse of the bubble, the temperature and pressure in the bubble can reach extremely high values (~3000 K, ~100 bar or even higher) that can cause decomposition of the solvent vapor entrapped in the bubble resulting in generation of extremely reactive radicals that can accelerate the kinetics of a chemical reaction.

Cavitation can occur at numerous locations in a fluid body simultaneously and can generate very high localized pressure and temperature. Cavitation also results in the generation of localized turbulence and liquid micro-circulation, enhancing mass transfer. Thus, mass transfer-limited reactions, endothermic reactions and reactions requiring extreme conditions can be effectively carried out using cavitation. Moreover, radicals generated during cavitation due to the homolytic dissociation of the bonds of molecules trapped in the cavitating bubbles or in the affected surrounding liquid, result in the occurrence of certain reactions.

The flow essentially undergoes a sudden contraction and expansion that generates essential pressure variation for the in-situ generation and collapse of either vapor or gas bubbles. As stated earlier, these bubbles undergo volume oscillations and a transient collapse, which can create cavitation effects by intense energy concentration that results in extremes of temperature and pressure and also intense convection due to micro-turbulence and shock waves. However, this effect is seen either inside the bubble (of initial size ~50-100 microns, which is compressed to about $\frac{1}{10}^{th}$ of its initial size) or in the bulk liquid in close proximity to the bubble. Thus, the energy concentration created by transient bubbles is on an extremely small time and temporal scale.

Through these contractions and expansions, the flow may get separated from the walls of the conduit. In this case, there is significant loss in the pressure head of the flow, which is manifested in terms of generation of turbulence in the flow. The turbulence creates fluctuations in the bulk pressure at low frequencies (1 to 2 kHz). These turbulent fluctuations are essentially superimposed over the mean pressure of the flow that keeps on increasing with the expansion of the flow. These fluctuations alter the behavior or pattern of radial motion of the cavitation bubble. In this case, the bubble undergoes an explosive growth followed by a transient implosive collapse. The cavitation effect produced by these bubbles is several folds higher than the bubbles in simple venturies. The difference in the cavitation bubble behavior in a orifice flow and in a venturi flow has been studied at length. (VS Moholkar and AB Pandit, Chemical Engineering Science, 2001).

In homogenous reactions, both the reagents and products remain in the same phase. The mechanical effects of cavitation play a smaller part in such reactions in comparison with the creation of high-energy intermediates. In heterogeneous reactions, cavitation bubbles collapsing at or near the phasic interface causes vigorous mixing. The surface area available for the reaction between the phases is significantly increased, thus improving the rate of reaction.

TABLE 1

Comparison of energy efficiency for different methods.

| Method | Time, min | Yield, % | Yield/energy, $kJ^{-1}$ |
|---|---|---|---|
| Acoustic | 10 | 99 | $8.6 \times 10^{-5}$ |
| Conventional with stirring | 180 | 98 | $2.7 \times 10^{-5}$ |
| Presented flow-through | 8 | 99.9 | $2.6 \times 10^{-3}$ |

It can be seen from Table 1 that reactions that take place in a flow through cavitation generator are correspondingly about 30 times and 100 times more efficient compared to acoustic cavitation the agitation/heating/refluxing method.

Accordingly, there is a need for a method to carry out heterogeneous reactions that does not require a large amount of energy input. Further, there is a need for such a method that avoids potentially dangerous, high-pressure operation. Furthermore, there is a need for an improve method of producing alcohol from biomass that is more efficient and more cost effective. The present invention fulfills these needs and provides further related advantages through the utilization of hydrodynamic flow-through cavitation and the chemical and physical reactions and process involved.

SUMMARY OF THE INVENTION

The method described herein does not require high energy input as the cavitation device is static, i.e., it does not contain moving parts. The apparatus simply requires a minimum input fluid velocity and pressure to create cavitation in the flow towards the goal of creating new products.

The present invention is directed to a process for extracting carbohydrates from biomass. The process begins with preparing the biomass for the extraction of carbohydrates. The preparation of the biomass may include washing, drying, chopping and/or grinding the biomass. The biomass may include corn cob, corn stover, cotton stalk, wheat straw, rice straw, sugarcane bagasse, switchgrass, poplar wood, sorghum straw, and/or water hyacinth.

A first biomass solution is formed by combining the prepared biomass with water, preferably demineralized, and an acid or an alkali. The demineralized water is added in a ratio of 10% to 50% w/v with the biomass. The acid preferably comprises sulfuric acid in the range of 1% to 5% v/v and the alkali preferably comprises sodium hydroxide in the range of 1% to 5% v/v. This first biomass solution is preferably thoroughly agitated to prevent settling of biomass particles.

The first biomass solution is subjected to a first hydrodynamic cavitation treatment. Acid or alkali hydrolysis of the biomass occurs during this first hydrodynamic cavitation treatment. The first biomass solution is preferably heated prior to the first hydrodynamic cavitation treatment; such heating by autoclaving, steam explosion or simple heat treatment. The first biomass solution exiting the first hydrodynamic cavitation treatment is filtered into a first filtrate and an intermediate biomass. The first filtrate contains extracted carbohydrates, typically pentose sugars.

A second biomass solution is created by combining the intermediate biomass with water, preferably demineralized, and an enzyme source. The demineralized water is added in a ratio of 10% to 50% w/v with the biomass. The enzyme source comprises cellulase enzymes, or microbes or fungi that release cellulase enzymes, the microbes comprising *Bacillus amyloliquefaciens* or *Bacillus subtilis* and the fungi comprising *Trichoderma reesei*. The process includes adjusting the pH of the second biomass solution to a desired pH for the enzyme source. The intermediate biomass is preferably washed and dried prior to creating this second biomass solution. The second biomass solution is preferably thoroughly agitated to prevent settling of biomass particles.

The second biomass solution is exposed to a second hydrodynamic cavitation treatment. Enzymatic hydrolysis of the biomass occurs during this second hydrodynamic cavitation treatment. The second biomass solution exiting the second hydrodynamic cavitation treatment is filtered into a second filtrate and a filtered biomass. The second filtrate contains extracted carbohydrates, typically hexose sugars.

A process for creating bioalcohol from the extracted carbohydrates includes combining the first filtrate with a bacterial species and nutrients to form a first fermentation substrate. The first fermentation substrate is fermented to form a first bioalcohol, which is separated from the first fermentation substrate using distillation, liquid-liquid extraction, gas sparging, or similar processes. Such a process also includes combining the second filtrate with a bacterial species and nutrients to form a second fermentation substrate. The second fermentation substrate is fermented to form a second bioalcohol, which is separated from the second fermentation substrate using distillation, liquid-liquid extraction, gas sparging, or similar processes. In a particularly preferred embodiment, the first filtrate and second filtrates are combined to form a blended filtrate, which blended filtrate is combined with a bacterial species and nutrients to form a blended fermentation substrate. The blended fermentation substrate is fermented to form a blended bioalcohol, which is separated from the blended fermentation substrate using distillation, liquid-liquid extraction, gas sparging, or similar processes. The bacterial species preferably comprise *Escherichia Coli*, *Saccharomyces cerevisiae*, *Zymomonas mobilis*, *Lactobacillus buchneri*, or *Clostridium acetobutylicum*, any of which may be genetically modified.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 14 is a cross-sectional view of the turbulizer disk taken along line 14-14 of FIG. 13.

FIG. 15 is a cross-sectional view of the radial multi-jet nozzle taken along lines 15-15 of FIG. 13.

FIG. 16 is a cross-sectional view of the cylindrical body taken along lines 16-16 of FIG. 13.

DETAILED DESCRIPTION OF THE PREFERRED EMBODIMENTS

Figure 1:
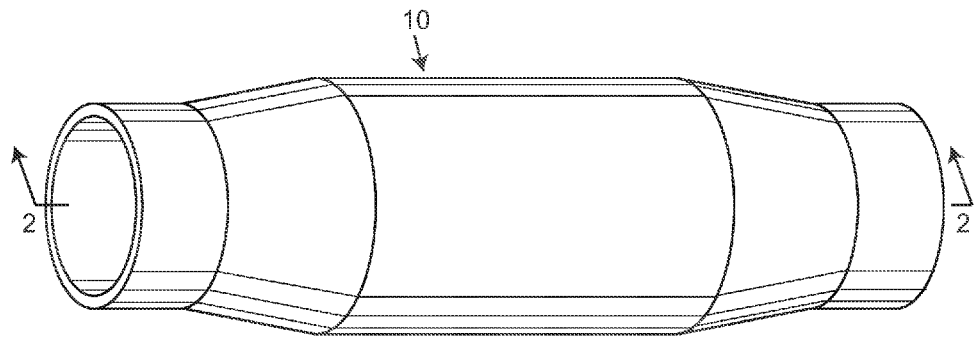
FIG. 1 is a perspective view depicting a preferred embodiment of a multi-stage cavitation device of the present invention.

The present invention is directed to a device and method for processing a fluidic reaction mixture via a hydrodynamic cavitation process with the result being the creation of new products. The reaction components inside the apparatus are influenced by pressure impulses and other features of controlled advanced hydrodynamic cavitation. The device and method herein described follows the aforementioned chemical reactions and processes such that the device stimulates cavitation in hydrodynamic liquids to the point where the end result is increased yield and quality of products.

A multi-step process for producing biofuel, in particular bioalcohol, using hydrodynamic cavitation is disclosed herein. More particularly, the multi-step process includes: (1) a process for the extraction of carbohydrates from biomass using hydrodynamic cavitation; and (2) a process for converting the carbohydrates into a bioalcohol using hydrodynamic cavitation.

The hydrodynamic cavitation device described herein is highly versatile for the extraction of carbohydrates from ligno-cellulosic biomass (or the biomass pretreatment), which is an important and cost-intensive step in the synthesis of (alcoholic) biofuels, especially through the fermentation (or biochemical) route. Hydrodynamic cavitation is useful in the pretreatment of biomass prior to synthesis of biofuels—primarily through fermentation. Such processing enhances the release of carbohydrates or sugars from biomass prior to fermentation of hydrolyzate (comprising of hexose and pentose sugars).

Hydrodynamic cavitation can be applied during pretreatment of the biomass, especially chemical pretreatment such as with dilute acid or dilute alkali. These pretreatments are applied prior to the enzymatic hydrolysis of cellulose in the biomass. The pretreatment has a two-fold purpose: (1) to break down the shield formed by lignin and hemicellulose which results in better and higher accessibility of enzymes to the cellulose during enzyme hydrolysis; and (2) to reduce the degree of polymerization of cellulose with disruption of crystalline structure, which enhances the yield of the enzymatic hydrolysis. The ligno-cellulosic biomass is typically in the form of agro- or forest residue. Biomass pretreatment is perhaps the most cost intensive step in overall biofuels synthesis. Obviously, any advancement of the pretreatment technology would have a significant impact on the economics of biofuels.

Prior to chemical pretreatment, the biomass is subject to a physical treatment such as mechanical comminution (reduction of particle size in order to increase surface area), steam explosion or autoclaving and/or liquid hot water pretreatment. During these pretreatments, the hemicellulose is hydrolyzed by acids released from the biomass. Hot water can have acidic properties at high temperatures that assist or catalyze the hemicellulose hydrolysis. These treatments cause the biomass to undergo rapid thermal expansion, which leads to opening up of the biomass particle structure and an increase in pore volume.

The chemical pretreatment is essentially aimed at enhancing the biodegradability of cellulose by removing the lignin and hemicellulose, and also to decrease the degree of polymerization and crystallinity of the cellulose component. The most common techniques that are applied are dilute acid pretreatment; dilute alkali pretreatment and ammonia fiber explosion. In the dilute acid treatment, several different acids like dilute sulfuric acid, dilute nitric acid or dilute phosphoric acid may be used.

Dilute acid pretreatment results in solubilization of hemicellulose while keeping the lignin and cellulose intact, which results in enhancement of enzymatic digestibility of cellulose. In this process, the oligomeric hemicellulosic saccharide can be hydrolyzed (almost to completion, depending on processing conditions) into monosaccharides. Nonetheless, dilute acid may cause degradation of some sugar molecules into furfural. Dilute acid treatment results in a high yield of pentose sugars like xylose. The addition of acid into the reaction mixture could be in homogeneous form or heterogeneous form such as an ion exchange resin. Recently, some have used Amberlyst-TM (15) ion exchange resin as a catalyst for hydrolyzing carbohydrates from macroalgae *Eucheuma cottonii* to extract simple sugars prior to fermentation.

The inventive cavitation device can also be used for the dilute acid pretreatment of biomass to release pentose carbohydrates and sugars. The addition of dilute acid (the most widely used acid being the sulfuric acid) gives effective hydrolysis. However, this acid itself has corrosive effects, and hence, the material from which the cavitation device is constructed needs to be suitably selected. Otherwise a corrosion resistant coating such as PTFE can be applied to the walls of the flow conduit. The pump used with the hydrodynamic cavitation device needs to have a sufficiently high discharge pressure to pump the process fluid.

For an alkaline pretreatment, various bases are used which primarily include dilute sodium or potassium hydroxide, calcium hydroxide, aqueous ammonia or ammonium hydroxide. Alkaline pretreatment results in delignification of biomass, which also results in solubilization of hemicellulose. The chemical mechanism underlying this is essentially saponification of intermolecular ester bonds cross-linking xylan hemicelluloses and other components like lignin. The alkaline pretreatment of lignocellulosic biomass has several beneficial effects such as increased internal surface area due to swelling, decreased degree of polymerization and reduced crystallinity. Moreover, alkaline pretreatment also disrupts the lignin structure and also separates the linkages between lignin and carbohydrates. Similar to the dilute acid pretreatment, the alkali can be added to the mixture of biomass and water before being subjected to the treatment in a hydrodynamic cavitation device.

An alternate method of providing catalyst in the reaction system is to coat the walls of the conduits with certain metal oxides (especially alkali metals such as calcium oxide) or mixed metal oxides (alkali metal oxide+alkaline earth metal oxides, such as calcium oxide+barium oxide or calcium oxide+barium oxide+strontium oxide). In acid hydrolysis, the walls could be coated with an ion exchange resin (in the form of a polymer film). These coatings can provide the necessary catalytic effect i.e. supplying of $H^+$ or $OH^-$ ions needed for hydrolysis. In this configuration, the undesired effects of corrosion due to homogenous acid or alkali catalyst can also be avoided. The turbulence present in the cavitating flow can assist faster and efficient transfer of the ions generated at the walls of the conduit due to interaction of the flow with the coated catalyst.

Hydrolysis of the biomass is essentially a mass transfer controlled process. The long chain cellulose molecules present in the biomass are less soluble in water than the short chain oligomers formed as intermediates during the hydrolysis. The solubility of both long and short chain molecules decreases with temperature. With sufficient and continuous flow of liquid through the reaction mixture, the more soluble molecules are removed which facilitates further dissolution of less soluble molecules. This process not only enhances sugar recovery but also reduces the degradation of sugars at the reaction conditions. If the more soluble oligomers are not removed, they are likely to precipitate back onto the surface of the biomass, especially with decreasing temperature of the reaction mixture after processing. Reactive lignin and sugar degradation products can also promote reattachment of cellulose, hemicellulose, and their oligomers, as well as, lignin, back to the solid biomass. These components may also form complexes with monomeric sugar if not removed.

The occurrence of transient cavitation in the reaction mixture generates intense microturbulence that removes and refreshes the water in the close packed biomass matrix. This assists in the efficient removal of localized sugar molecules formed within the biomass matrix. The sonochemical effect, i.e., the generation of highly reactive radicals due to the transient collapse of bubbles, does not contribute much to the enhancement of sugar or carbohydrate release from the biomass. This is, in part, because most of the hydrolysis reaction occurs through $H^+/OH^-$ ions in the solution provided by the acid/alkali.

Numerical simulations of cavitation bubble dynamics in flow through constrictions show the formation of strong microturbulence and high intensity shock waves during the transient bubble motion in cavitating flow through nozzles, venture, or the like. The exact dimensions of the constriction are decided by the capacity of the overall unit and may change with the capacity. In such mathematical models, the vapor transport in the cavitation bubble during radial motion is hypothesized to be a diffusion limited process. The diffusion limited model is as follows: The expansion of the cavitation bubble is accompanied by the evaporation of an ever increasing quantity of solvent vapor (water in the case of biomass hydrolysis) at the bubble wall. These vapor molecules diffuse into the core of the bubble. During the ensuing collapse phase, the vapor molecules diffuse back out to the bubble wall and condense.

In the final moments of bubble collapse, the bubble wall velocity becomes extremely fast (sometimes even exceeding the speed of sound). At the moment of collapse, the time scale of diffusion of vapor in the bubble towards the bubble wall exceeds the time scale of bubble motion. The vapor thus becomes "frozen" or entrapped in the bubble. Due to the extremely rapid motion of the bubble wall, the condensation of the vapor molecules that manage to reach the bubble wall is not in equilibrium (i.e. not all vapor molecules undergo condensation and phase change due to small accommodation coefficient). This further contributes to entrapment of the solvent vapor in the bubble. The entrapped vapor is then subjected to extreme conditions of temperature and pressure generated at the final stage of bubble collapse, when the bubble size is at its minimum during the radial motion. At these conditions, the vapor molecules undergo thermal dissociation to generate numerous species, some of which are radical species.

With reference to the attached drawings, FIGS. 1-6, a device for the creation of cavitation processes in fluid flows resulting in localized regions of increased pressure, heat release and vigorous mixing to generate changes in fluids are disclosed. The method and device include the use of a flow-through hydrodynamic multi-stage cavitation reactor to promote chemical and physical processes and reactions that occur in a short time and results in new products. Intense localized heat released because of gas compression and microjet formation, which accompany the implosion of cavitation bubbles, excite molecules contained in vapors and in the adjacent layers of surrounding fluid transiently enriched with the high-boiling point ingredient(s), thereby driving chemical reactions and processes.

Figure 2:
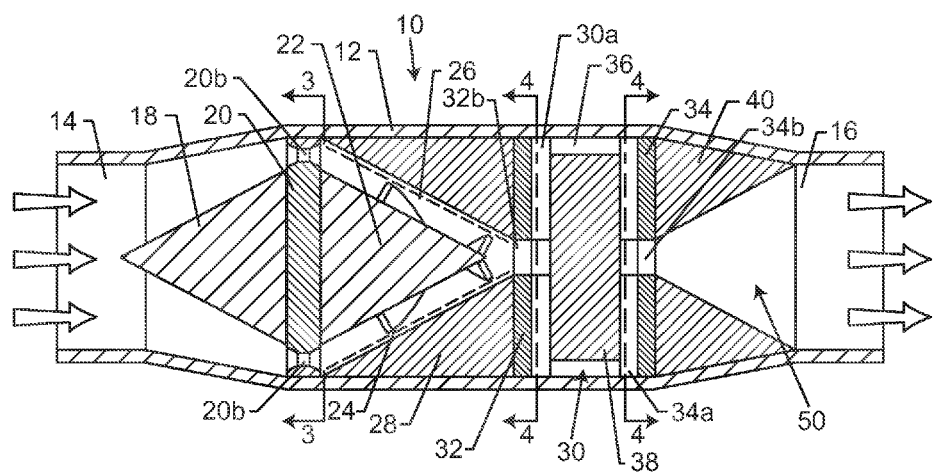
FIG. 2 is a cross-sectional view of the multi-stage cavitation device taken along line 2-2 of FIG. 1.
Figure 3:
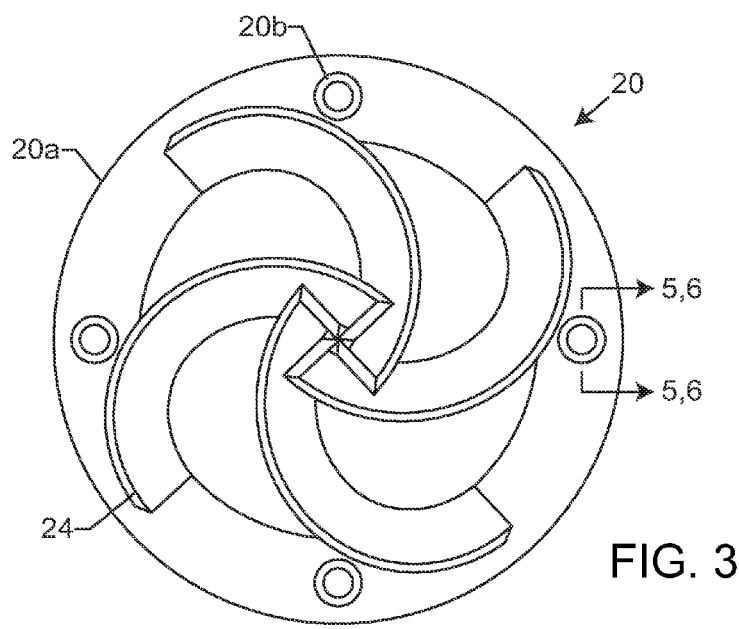
FIG. 3 is a cross-sectional view of the working chamber of the cavitation system taken along line 3-3 in FIG. 2.
Figure 4:
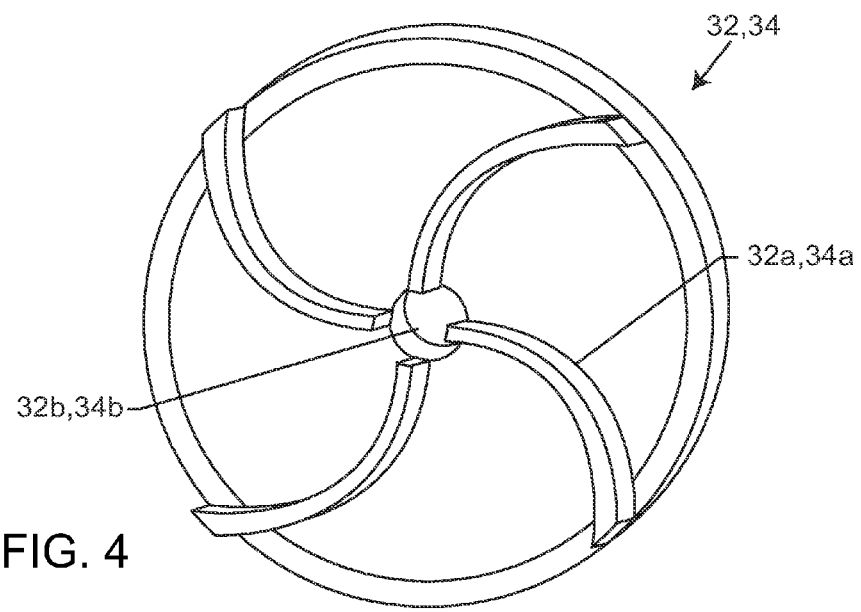
FIG. 4 is a cross-sectional view of the vortex element taken along lines 4-4 in FIG. 2.

A preferred embodiment of the multi-stage cavitation device of the present invention is illustrated in FIGS. 1 and 2, which depict a hydrodynamic flow-through multi-stage cavitation device 10 capable of achieving the objects of the present invention. Said device 10 comprises a housing 12 defining a substantially cylindrical exterior having a fluid inlet 14 and a fluid outlet 16. The fluid inlet 14 is positioned to introduce the fluid medium into the device 10. Between the fluid inlet 14 and the fluid outlet 16 are a series of chambers, as described below, configured to create cavitational features in the fluid medium. The fluid outlet 16 directs the fluid medium from the device 10.

Figure 5:
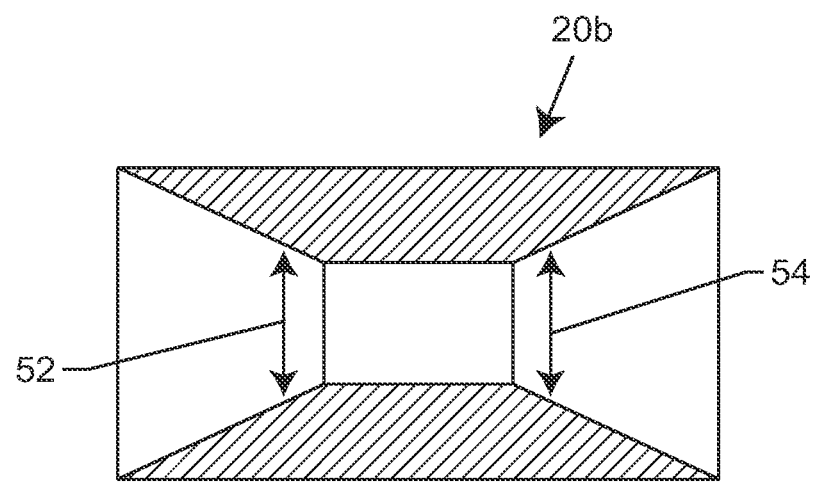
FIG. 5 is a cross-sectional view of one embodiment of a channel in a multi-jet nozzle taken along line 5-5 in FIG. 3.
Figure 6:
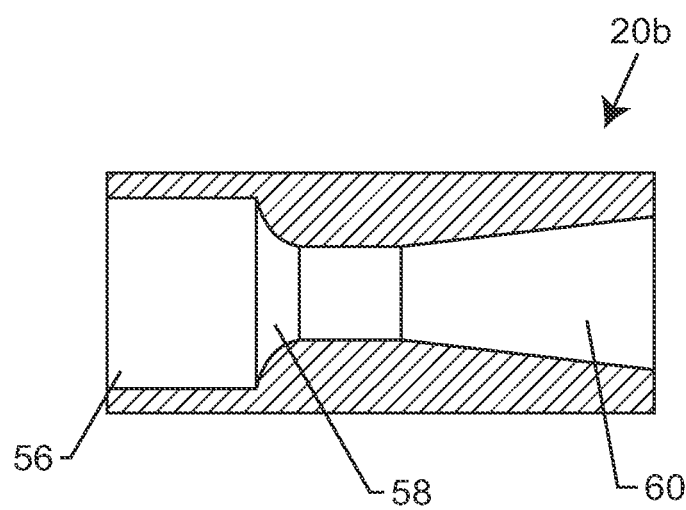
FIG. 6 is a cross-sectional view of an alternate embodiment of a channel in a multi-jet nozzle taken along line 6-6 in FIG. 3.

The cavitation device 10 as shown in FIGS. 1 and 2 is comprised of a cylindrical body 12 made preferably of a metal, an inlet 14 and an outlet 16. An inlet cone 18 is located in front of a multi-jet nozzle 20 along the flow path. A guide cone 22 is positioned behind the nozzle 20 and features spiral guides 24. The multi-jet nozzle 20 is shaped as a disk having a perimeter ring 20a and features four channels 20b that have abrupt contractions and expansions across their width (FIGS. 5 and 6). The number of spiral guides 24 is equal to the number of channels 20b in the multi-jet nozzle 20. The channels 20b are uniformly distributed throughout the surface area of the perimeter ring 20a and direct flow into a working chamber 26.

The working chamber 26 is located behind the multi-jet nozzle 20 along the flow path and has an inner wall formed by the guide cone 22 and an outer wall formed by a convergent cone 28. The convergent cone 28 is aligned coaxially with the guide cone 22. Behind the convergent cone 28 is the vortex chamber or generator 30 comprised of disks 32, 34 with curved flow guides 332a, 34a and central holes 32b, 34b (FIG. 4) that are coaxially aligned. An annular gap 36 is located between the front and rear disks 32, 34 and around a cylinder-type body 38 of slightly smaller diameter than the vortex chamber 30. The curved flow guides 32a, 34a are raised with respect to the disks 32, 34 so as to extend out to the cylinder type body 38. The body 38 blocks the direct path of the fluid flow jet emerging from the central hole 32b in the front disk 32.

The flow guides 32a, 34a create multiple curved flow paths from the central hole 32b in the front disk 32 to the annular gap 36 of the vortex generator 30. Similar paths are created from the annular gap 36 to the central hole 34b on the rear disk 34 on the backside of the cylinder-type body 38. The central holes 32b, 34b, the outlet of the convergent cone 28 and an inlet of an atomizing cone 40, which is situated behind the vortex generator 30 along the flow path, all have the same diameters.

The inventive cavitation device 10 can be made from many materials, although there are some constraints placed on them. The materials should be simple in fabricating and brazing, be able to withstand both high pressure and high temperature, and exhibit high resistance to corrosion, thus allowing the system to be operated continuously and/or repeatedly with a variety of fluids. The materials should be mechanically compatible to assure similar properties of material extension upon heating. A coating with alloys, electrodeposited layer(s), plastics, nanoparticles, nanodiamond, metals, catalysts and enzymes is possible. In one preferred embodiment of the invention, the device is made from a hardened stainless steel.

Both the inner and outer system dimensions depend upon the intended use of the device. A small-scale cavitation system is preferable when the amount of fluid to be processed is limited or its cost is too high. A large system with an inner diameter of ten inches or greater provides a high treatment throughput and may generate larger cavitation features. In the preferred embodiment, the cavitation device 10 is about fourteen inches long with an outside diameter of about three inches.

The present cavitation system provides at least three major cavitation zones and operates as follows. Presumably sufficient fluid is initially pressurized with a proper pressure pump and introduced through the inlet 14 which has a uniform outside diameter of one and one-half inches in the preferred embodiment. The fluidic reaction mixture enters at the top of the inlet cone 18, which is surrounded by the inner peripheral wall of the housing 12. The fluid accelerates over the inlet cone 18 and moves into the channels 20b of the multi-jet nozzle 20. To enhance mixing and cavitation, the channels 20b of the multi-jet nozzle 20 are uniquely shaped and contain both contractions 52 and expansions 54. More particularly, the cross-sectional diameters of the channels 20b vary along the fluid path, as illustrated in FIG. 5.

As illustrated in FIG. 6, the channels 20b can alternately be fabricated as Venturi nozzles to separate vortices and generate pressure pulsations at characteristic frequencies. A Venturi nozzle is defined as a throttle device comprised of a conical inlet 56 with a round profile, a cylindrical throat 58 and a conical outlet (diffusor) 60. The Venturi nozzle generates unsteady flow that can be calculated (Fedotkin and Gulyi, 2000; Mahesh et al., 2004; Li et al., 2008).

When fluid moves through the channels 20b, the vortices, completely detached jets and possible cavitation are produced. They act upon the fluid by altering its properties. The streams exiting adjacent channels 20b are mixed by passing through the narrow gaps formed by the spiral guides 24 mounted between the guide cone 22 and the walls of the convergent cone 28, and flowing through the working chamber 26.

Although this configuration is preferred, it should be understood that the spiral guides 24 do not have to be mounted at a specific angle or at a specific location relative to the channels 20b in order to generate cavitation within working chamber 26. The preferred configuration of the guides 24 has a gradual decrease in the pitch of the spiral toward the peak of the guide cone 22 in order to accelerate the flow velocity. This allows the fluid to form patterns and jets in the flow and form vortices and shear when the flow's upper layers separate from those lying underneath because of the substantial difference in the velocities.

The fluid directed by the guides 24 exhibits significant cavitation within the working chamber 26. Implosion of the generated cavities results in the formation of shock waves, high-velocity local jets and heat dissipation, improving both reaction rates and mass transfer. The jet velocities and intensity of the vortices and cavitation depend on the interaction of a fluid-vapor mixture with vapor. As the cavitation number decreases, fluctuating cavities with periodic vortex shedding, fluid-vapor filled cavities within a turbulent wake, and cavities filled with vapor are observed. In the cavitation region, strong momentum transfer between the higher and lower flow layers occurs. In the core zone of the region, the flow velocity is high and evenly distributed. The low velocity region lessens as the flow path moves downstream. The cavitation bubble dimensions and the intensity of the cavitation field increase as the fluid moves toward the middle part of the working chamber 26. An increase in the difference in flow pressures favors cavitation and vortex formation.

The cross-sectional area of the working chamber 26 decreases along the flow path due to the decrease in diameter of the guide cone 22, and the corresponding diameter of the convergent cone 28 resulting in acceleration of the fluid flow. With the increase in velocity the fluid pressure drops, favoring conditions suitable for cavitation. Moreover, upon exiting the working chamber 26, the fluid is further accelerated by sliding over the spiral guides 24. The fluid then passes into the vortex chamber 30 through the central hole 32b in the front disk 32, enters the flow guides 32b and passes to the annular gap 36. The fluid then follows the flow guides 34a of the rear disk 34 to the central hole 34b. The drastic increase in the cross-sectional area of the flow path, sharp changes of the flow direction and vigorous vortex formation promote nucleation, growth and coalescence of cavitation features. In the vortex chamber 30, the cavitation bubbles are subjected to the increased pressure caused by flow dynamics, i.e., apparent centrifugal and Coriolis forces. Consequently, the bubbles implode at a higher flow velocity than normal.

Near exiting the vortex chamber 30, the fluid, which has been heated by the cavitation process, enters the channels formed by the guides 34a and accelerates due to the narrowing cross-sectional area. When fluid moves along the curved channels, it causes rolling friction, which requires much less force to overcome than sliding friction. The flow guides 32a, 34a of the disks 32, 34 of the vortex generator 30 are shaped as curved arcs of circles in order to reduce the energy required to direct fluid in the vortex generator 30. The energy required to force flow along the convex section of the curved guides 32a, 34a is much less than with straight guides. The force required for overcoming the rolling friction on the concave section of the guides 32a, 34a depends on their curvature.

The vortex flow exits the central hole 34b in the rear disk 34 and atomizes within the cone 40. The drastic increase in cross-sectional area, sharp alterations of the flow direction and its vortex nature promote formation and expansion of cavitation features and other effects. In the outlet 16 from the atomizer 50, the flow rate drops with minimal energy loss until it reaches the level acceptable by the downstream pipe line safety requirements. As the hydrostatic pressure rises, the cavitation bubbles quickly collapse and the negative impact of cavitation on the downstream pipe line and equipment promptly disappear. The flow-through cavitation process may be coupled with UV-Vis-IR light treatments to improve efficiency. The fluid may also be irradiated with sound or ultrasound waves prior to, during and/or after the flow-through cavitation treatment.

The present multi-stage cavitation device 10 provides at least three zones where vigorous vortex formation and intense cavitation occur. The first cavitation zone is within the working chamber 26, the second cavitation zone is in the vortex generator 30, and the third cavitation zone is in the atomizing cone 40. This configuration is particularly cost efficient in a large volume treatment. However, the same principles can be applied to any alteration at smaller scale. Note, that ultrasonic radiation generating devices are not sufficient to induce uniform cavitation in large vessels.

Figure 7:
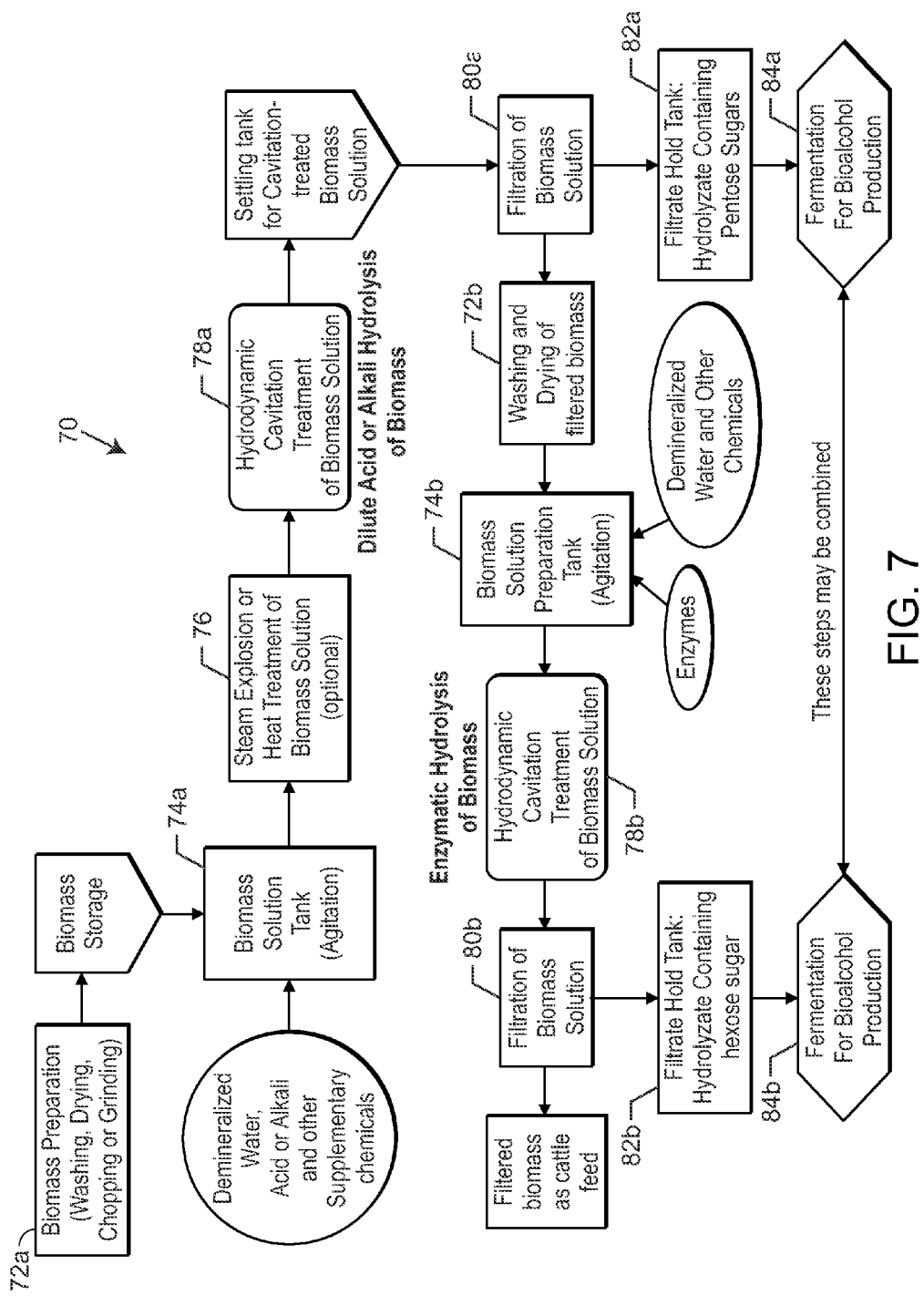
FIG. 7 is a flowchart illustrating the processes for extracting carbohydrates from biomass and converting those carbohydrates into bioalcohol.
Figure 8:
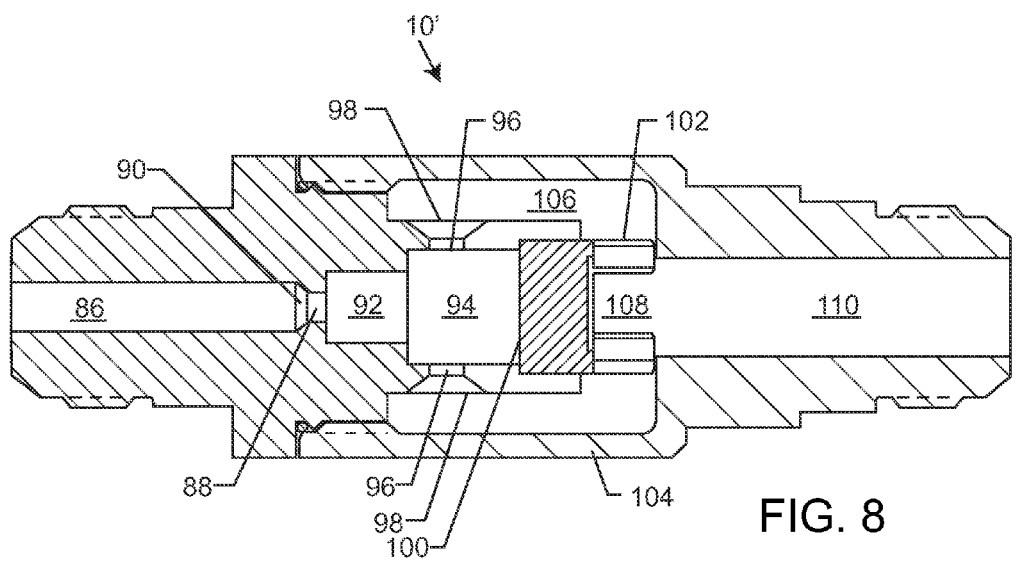
FIG. 8 is a cross-sectional view of an alternate embodiment of the cavitation device of the present invention.
Figure 9:
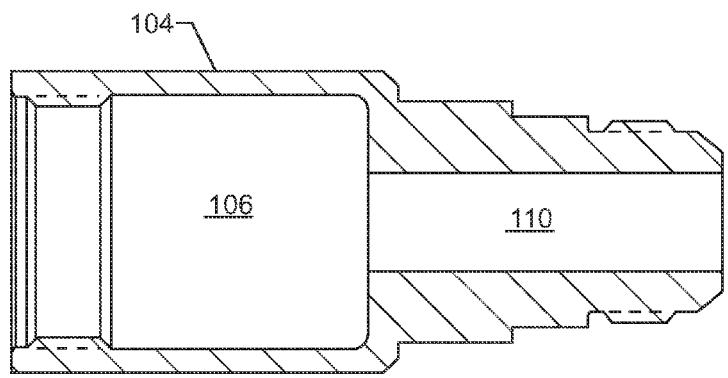
FIG. 9 is a cross-sectional view of an outlet portion of the cavitation device depicted in FIG. 8.
Figure 10:
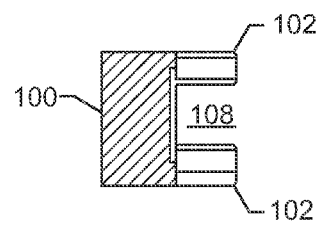
FIG. 10 is a side, cross-sectional view of the impact pad of the cavitation device of FIG. 8.
Figure 11:
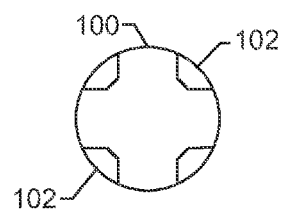
FIG. 11 is an end view of the impact pad of the cavitation device of FIG. 8.

The device 10 schematically presented in FIGS. 1-6 is used for carrying out the method, according to the present invention. FIG. 7 illustrates a flowchart of the inventive processes for extracting carbohydrates from biomass and converting said carbohydrates into bioalcohol. The process 70 begins with the step of first biomass preparation 72a. The first biomass preparation 72a includes washing, drying, chopping and/or grinding the biomass material to remove unwanted contaminants and reduce its particle size. The biomass is preferably lignocellulosic biomass—available mainly as agro-waste or forest-waste. Typical biomass materials include corn cob, corn stover, cotton stalk, wheat straw, rice straw, sugarcane bagasse, switchgrass, poplar wood, sorghum straw, and water hyacinth. Preparation 72a typically includes separation of unwanted parts, i.e., roots, etc., washing with water, drying at about 50-60° C. and then chopping or grinding into small pieces. The desired size of biomass pieces is typically between 1 mm to 5 mm. The prepared biomass is then stored in a hopper or similar container until it is ready to be subjected to further processing.

A first biomass solution is mixed 74a containing the prepared biomass and reagents. The reagents include water and an acid or an alkali, as well as, other supplementary chemicals. The water is preferably demineralized. The mixture is usually prepared in a tank of suitable dimensions preferably provided with suitable agitation, i.e., a pitched blade turbine or similar operated at about 100-500 rpms. The tank is filled with demineralized water and the processed biomass is added from its hopper. The proportion of biomass to water is determined by weight or volume—typically 10-50% w/v. Either an acid ($H_2SO_4$) or an alkali (NaOH) is added in required proportions by percent volume of water. For acid the range is 1-5% v/v. The alkali may be added to form a solution of similar strength. The solution is preferably thoroughly agitated to achieve a well-blended solution.

The first biomass solution may optionally be subjected to autoclaving, steam explosion or heat treatment 76. Autoclaving or steam explosion is by heating to about 120° C. under 15 psi steam pressure. Heating under pressure results in thermal expansion of the biomass, which increases its porosity. Such expansion is helpful in faster diffusion of enzyme molecules through the biomass matrix and provides easier access to the cellulose portion of the biomass. Heat treatment is simple heating to a temperature of about 100° C.

If the heating step 76 is carried out under acidic conditions, it also results in acidic hydrolysis of the hemicellulose portion of the biomass. This releases a significant amount of pentose sugars like xylose. Some of the cellulosic portion may also get hydrolyzed to release hexose sugars if the acid concentration is sufficiently high. Some similar hydrolysis will also occur during alkaline treatment, but on a much smaller scale. Alkaline pretreatment results in removal of the lignin layer that exposes the hemicellulosic and cellulosic portions of the biomass to enzyme action. The biomass may again be stored after heat treatment 76, but must be frequently agitated to avoid settling of biomass particles.

The solution—either with or without the heat treatment process 76—is then subjected to a first hydrodynamic cavitation treatment 78a using a device similar to those described elsewhere herein. A slurry pump of suitable capacity must be used and the biomass solution is preferably recirculated through the hydrodynamic cavitation device using a holding tank. The temperature of the solution will rise as it is processed through the cavitation device, which provides additional heat treatment. Hydrolysis of hemicellulose and cellulose occurs during this first cavitation treatment 78a. A large portion of the carbohydrates are extracted from the biomass by an acid or alkali hydrolysis process, which process is aided by the hydrodynamic cavitation. Strong microturbulence generated by hydrodynamic cavitation helps in the faster and more efficient transport of sugar moieties out of the biomass matrix into the solution. The time and intensity of the treatment 78a depends upon the biomass. A typical treatment 78a of about 30 minutes should be sufficient to remove all sugar released from hydrolysis.

The cavitated biomass solution is sent to a settling tank and subjected to a first filtration process 80a using suitable filters to separate the biomass from the solution containing the extracted carbohydrates. The first filtrate containing the extracted carbohydrates, typically pentose sugars—is sent 82a to a first holding tank for later fermentation. The filtered biomass is subjected to a second biomass preparation process 72b, wherein it is again washed, preferably repeatedly to remove all acid and alkali, and the dried and stored for further hydrolysis.

The second processed biomass is then combined with enzymes, water—preferably demineralized—and other chemicals to form a second biomass solution 74b. The solution of biomass and demineralized water is prepared in a concentration of about 10% w/v. The enzymes may comprise commercial Cellulase enzymes, or microbes (i.e., *Bacillus amyloliquefaciens* or *Bacillus subtilis*) or fungi (i.e., *Trichoderma reesei*) that release such enzymes. In the case of commercial enzymes, they may be added to the biomass solution. In the case of microbes or fungi, an inoculum along with supplementary nutrients may be added to the biomass solution. The pH of the solution is preferably adjusted to a pre-determined value using buffer solutions or the addition of simple acids ($H_2SO_4$) and alkalis (NaOH). In the case of commercial enzymes, the optimum pH is already provided by the supplier. For microbial hydrolysis, some experimentation is needed to determine the optimum pH. This second biomass solution 74b is also agitated during mixing as described above to prepare a well-blended solution.

This second biomass solution is then subjected to a second hydrodynamic cavitation treatment 78b to extract further carbohydrates by enzymatic hydrolysis. The conditions of this second cavitation treatment 78b are much more mild that the conditions of the first cavitation treatment 78a. This is because the enzyme molecules or microbial cells are delicate and can be easily denatured or disrupted due to the shockwaves produced by cavitation bubbles or high shear stress in the flow. While a slurry pump is again used, the discharge pressure should be small—typically in the range of 3 to 5 bar. In this second hydrodynamic cavitation treatment 78b, the cavitation device is operated essentially to provide convection in the flow to enhance the transport of enzyme molecules in the biomass matrix and their access to the cellulose in the biomass. Such second cavitation treatment 78b preferably continues or is recirculated through a holding tank for about 30 minutes.

The second cavitated biomass solution is then subjected to a second filtration process 80b to separate the biomass from the hydrolyzate, i.e., solution containing the extracted carbohydrates. The second filtrate containing additional extracted carbohydrates—typically hexose sugars—is sent 82b to a second holding tank. The remaining filtered biomass may be stored for further use as fuel, cattle feed or other intended uses.

The first and second filtrates 82a, 82b, may be stored in separate holding tanks or the same holding tank. The first and second filtrates 82a, 8sb are subjected to fermentation processes 84a, 84b using suitable bacterial species to produce the bioalcohol. The fermentation processes 84a, 84b may be performed separately or together, i.e., as a single process. Whether fermentation is performed as a single process or two separate processes depends upon the requirements of the facility.

Typical fermentation processing last from about 72 to 96 hours. The hydrolyzate or filtrate 82a, 82b may be supplemented with nutrients for the growth of a microbial culture. Typical bacterial species includes *Escherichia Coli, Saccharomyces cerevisiae, Zymomonas mobilis*, and *Lactobacillus buchneri*. All of these species can consume both hexose and pentose sugars. Mixed sugar consumption is enhanced in genetically modified species. Use of such genetically modified species facilitates the simultaneous fermentation processing 84a, 84b of both filtrates 82a, 82b containing mainly pentose and hexose sugars, respectively. These species produce bioethanol. For biobutanol, one would use species *Clostridium acetobutylicum*, which is an anaerobic species. Many genetically modified versions of this species are also available.

Following fermentation, the alcohols are separated from the broth by standard distillation. Alternative processes to distillation include in-situ product recovery and removal using techniques such as liquid-liquid extraction or gas sparging.

In accordance with the present invention, the fluidic reaction mixture is treated either continuously or periodically, by passing through any of the cavitation devices disclosed herein. The devices can be placed anywhere in a production site or any other body. Another design exists in which the device may be fixed in position or movable. In addition, multiple devices may be combined in a series or parallel configuration. In practice, it is necessary to take into account the cost of the device, its production capacity and the energy, maintenance and operation cost. It should be emphasized, that an operator of the hydrodynamic cavitation device is not required to wear high performance safety products for hearing protection, such as earmuffs or earplugs, as would be in the case of high-frequency cavitation.

The cavitation devices are static, i.e., contain no moving parts, and are configured for operation at a set fluid velocity and pressure of fluid medium. As described below, the changing of chamber diameters and surface features within the devices causes the generation of cavitation fluid features, i.e., bubbles. The subsequent collapse of the cavitation bubbles results in the localized elevations of pressure and temperature and drives the extraction process at a higher rate to achieve a higher yield than other processes.

When fluid is subjected to the consecutive multi-stage cavitations it is heated up and becomes enriched with bubble nuclei. This lowers the downstream cavitation threshold, intensifies processing and allows selective chemical reactions to occur while targeting compounds of interest. This makes the present device unique and especially suitable for treatment of multi-component fluids such as, for example, mixtures of biomass with water, acids or bases.

The flow-through cavitation devices are preferably multi-stage apparatuses whereby components are manipulated through localized high pressure and temperature impulses and advanced gas phase to solid/liquid phase transfer principles. Hydrodynamic cavitation assumes formation of vapor bubbles within a fluid accelerated to a proper velocity. In practice, cavitation is achieved by forcing fluids into the flow-through hydrodynamic cavitation device accelerated with a high-pressure pump and/or by reducing the available flow cross-sectional area at constant pressure. The faster the flow rate, the lower the cavitation number. A lower cavitation number (especially cavitation numbers less than 1) equates to a higher degree of cavitation. The preferred embodiment of the present invention optimizes the cavitation to achieve the high reaction yield by applying the most suitable pump pressure selected from a preferred range of 25-5,000 psi. If too much energy is applied or the treatment time is too long, then the cost goes up. By applying hydrodynamic cavitation at a pump pressure designed to cause alcohol-filled bubble formation and chemical conversion consistently throughout the fluidic reaction mixture, proper changes take place and a desirable outcome is achieved.

The present invention uses energy released upon the implosion of cavitation bubbles to carry out mass transfer processes. Hydrodynamic cavitation is the phenomenon of the formation of vapor cavities in a flow of fluid, which is followed by the bubble collapse in a downstream high-pressure zone. In practice, the process is carried out as follows. The fluid flow is pumped into the cavitation device. In a constriction, the flow accelerates causing the pressure to drop. This pressure drop results in the formation of bubbles filled with the vapors of volatile compounds that boil under the given conditions, i.e., a cavitation zone. When the cavitation bubbles move beyond the boundary of the low-pressure zone, the pressure in the flow increases and the bubbles collapse, exposing the vapors found within them and the surrounding liquid layer to localized high pressure and temperature, shearing forces, shock waves, acoustic vibration and electromagnetic irradiation. Each cavitation bubble serves as an independent mini-reactor, in which chemical reactions and/or mass transfers occur, particularly at the vapor/liquid interface. The localized pressure and temperature are significantly higher than those found in many other industrial processes where the overall pressure and/or temperature may be increased rather than on a localized scale. The alteration of fluid composition results from the chemical reactions taking place within the collapsing bubbles and/or in the adjacent layers of fluid.

The phenomenon is named cavitation, because cavities form when the fluid pressure has been reduced to its vapor pressure. The vapor bubbles expand as they move and suddenly collapse, creating a region of high pressure. The occurrence of cavitation bubble implosion is accompanied by the formation of numerous deformed micro bubbles. The pressure and temperature of vapors contained in these bubbles are very high. As fluid enriched with these micro bubbles moves into a reduced pressure zone, the micro bubbles become nuclei, which are less stable than those originally present in the fluid, and expand. The cavitation bubbles developed from these nuclei enhance the cavitation field intensity. The continuous process of bubble multiplication, expansion and implosion lowers the cavitation threshold because cavitation bubbles grow from the vapor nuclei, whose volume is larger than that of the naturally present nuclei. The sudden collapse causes tremendous localized increases in pressure and temperature and intense shearing forces, resulting in high yield chemical reactions.

By subjecting the fluidic reaction mixture to hydrodynamic cavitation, reagent molecules are activated and are converted into new products.

The fluid directed through the device exhibits significant cavitation. The cavitation features created in the fluid flow include vapor bubbles of volatile components. As the velocity of fluid flow increases, its pressure drops. As the fluid pressure may drop below the vapor pressure of certain more volatile compounds, those compounds can form vapor bubbles. Those of ordinary skill in the art understand that more volatile components have boiling points significantly lower than the boiling points of other less volatile components that may initially be present or produced in the course of treatment. Given these significantly lower boiling points, the more volatile components will more readily form vapor bubbles at the reduced fluid pressures in the cavitation device than other less volatile components. The cavitation process may also create vapor bubbles from air or other gasses trapped in pockets or cavities along the inner surface of the device.

The processing is dependant upon the physical properties of the fluid being processed and the energy requirements based upon ambient conditions necessary to generate cavitation in the fluid. It is well known that the complex liquid mixture comprised of different chemical compounds can be separated into pure fractions by heating it to the temperature at which the individual fractions will evaporate (the procedure is called atmospheric fractionation distillation). Generally, the compounds can be efficiently separated by, for example, fractionation distillation at a pressure of 1 atm, if the difference in their boiling points is at least 25° C. Thus, there is no doubt that more volatile components will boil first under the conditions described in the proposed invention. These first boiling components form bubbles filled with vapors for providing increased contact area between the liquid oil and the gaseous alcohol for improved processing.

Implosion of the generated cavities results in the formation of shock waves, high-velocity local jets and heat dissipation, improving both mass transfer and reaction rate. As the cavitation number decreases, fluctuating cavities with periodic vortex shedding and vapor-filled cavities are observed. In the cavitation regions, strong momentum transfer between higher and lower flow layers occurs. The cavitation bubble dimensions and the intensity of the cavitation field increase as the fluid moves through the cavitation device. An increase in the difference in the flow pressures favors cavitation and vortex formation.

In the case of a cavitation treatment of a multi-component fluid, the composition of the cavitation bubbles differs from that of the fluid. The bubble composition is enriched with the vapors of the compounds that are volatile under the given conditions. The bubble implosion releases energy that drives chemical reactions and/or heats the fluid. The processed mixture contains the products of these reactions, i.e., the newly formed compounds. The size of cavities depends on the nature of the fluid under treatment, the engineering design of the cavitation device, and other conditions, such as the velocity of flow sustained by a pump. The pump pressure may be increased, as determined on a case-by-case basis, until a proper intensity of cavitation is achieved. In addition to determining the size, concentration and composition of the bubbles, and, as a consequence, the amount of energy released, the inlet pressure and device design govern the reaction outcome.

A practical approach to achieve the desired degree of cavitation is to establish a pressure that provides enough bubble implosion energy for mixing and carrying out the reactions. The optimal pressures produce bubbles in sufficient quantities to achieve a high yield. However, as one skilled in the art would understand, different reaction mixtures require different energies obtained through cavitation in order for their products to form. Energy released because of bubble implosion during a flow-through hydrodynamic cavitation process activates molecules forcing them to react and form new compounds.

From an overall point of view, the processing in the cavitation apparatus occurs at ambient temperature and ambient pressure. No heat is added during the cavitation processing, although pre-heating may occur. The cavitation-assisted reaction is run at pump pressures between 25-5,000 psi, ideally at around 500 psi.

The cavitation apparatus creates conditions for a relatively instantaneous process due to the high-energy state of the gas-phase molecules, vigorous mixing and the high reactivity of heated solid/liquid-phase molecules. Extraction of carbohydrates is completed in seconds or even faster than that after a single pass through the cavitation device, although multiple passes are possible.

It is important to note that the method of the claimed invention is designed to operate in a continuous manner as the fluid flow is pumped through the cavitation device. Most prior art disclosures include cavitation systems that comprise batch or hybrid batch/continuous systems. In such prior art systems, the reagents are introduced to the system and the reaction is allowed to proceed to equilibrium in a residence chamber/vat. Once equilibrium is achieved, a portion of the products are removed from the system so that the remaining reagents and any subsequently added reagents may react to establish a new equilibrium. Such prior art processes require a long residence time, in some cases many hours, in order to produce the desired yield.

This is especially important in extraction processes such as this where the liquid in a solid/liquid interface around a particular area of the biomass may become saturated with carbohydrates and prevent the extraction of further carbohydrates until the liquid is changed. The higher the concentration of products, i.e., carbohydrates, the slower the rate of extraction. This makes the prior art methods time consuming, expensive, and less efficient when compared to the claimed method with a comparatively faster extraction process with a high-yield.

Further, the prior art methods disclose a method wherein all components are present in the solid/liquid phases. In contrast, the generation of cavitation features by the claimed process results in the formation of transient gas bubbles comprised of volatile components to improve mass transfer and extraction of carbohydrates. This gas-solid/liquid reaction produces a faster and greater yield over the solid/liquid reaction of the prior art batch systems. The inventors are not aware of any preexisting teaching or disclosure of a similar gas-solid/liquid extraction process for the extraction of carbohydrates from biomass. The gas-solid/liquid interface at the surface of each vapor-filled micro bubble provides a very large interphase reaction surface, superior mixing, and allows for the prompt separation of products.

The present invention makes it possible to carry out accelerated cavitation-assisted carbohydrate extraction processes by causing the repeated generation and subsequent collapse of cavitation bubbles. The invention also allows for the extraction of carbohydrates without consuming large amounts of energy and avoids high-pressure operations. The present invention can extract carbohydrates and produce bioalcohol in a more efficient and more cost effective manner.

An alternate embodiment for the cavitation device, illustrated in FIGS. 8 to 11, presents a cavitation device 10' made of stainless steel and having a generally cylindrical shape. It is assembled of at least three parts and is provided with threads at the outer surfaces of the inlet and outlet ends for installation in line. Fluidic mixture is fed in to the cavitation device 10' with a pump operating at the pressure that allows sustaining the selective generation of cavitation bubbles composed of alcohol vapors. The fluidic mixture flows through a first cylindrical passage 86 and enters a short downstream cylindrical passageway 88 having a smaller diameter and connected to the first cylindrical passage 86 with a conical opening 90. The fluid flow then enters third and fourth cylindrical passages 92, 94 of progressively larger diameters.

The fourth cylindrical passage 94 has two cylindrical passage openings 96 in its wall each interconnected to an inverted conical passageway 98. In addition, the fourth cylindrical passage 94 is provided with a downstream cylindrical impact pad 100 that has four segments of circumferential wall 102 on its top surface. (FIGS. 10 and 11) The fourth cylindrical passage 94 and impact pad 100 are surrounded by an outer housing 104 that creates an annular chamber 106. The gaps 108 between the wall segments 102 on the top surface of the impact pad 100 connect the annular chamber 106 to an outlet chamber 110. The fluid flow exhibits turbulence when it encounters the bottom surface of the impact pad 100, accelerates passing through the two small openings 96 in the wall of the fourth cylindrical passageway 94, entering annular chamber 106. The fluid flow then moves through annular chamber 106 towards the gaps 108 located between the four segments of the circumferential wall 102 on the top surface of the impact pad 100 where the high-energy jets collide and enter the outlet chamber 110 with a diameter that is smaller than the diameter of the fourth cylindrical passage 94. As the fluidic mixture of biolipid, low molecular weight alcohol and catalyst moves along the passageways of the cavitation device 10', it undergoes multiple cavitation events due to selective alcohol vaporization and subsequent bubble implosion.

Figure 12:
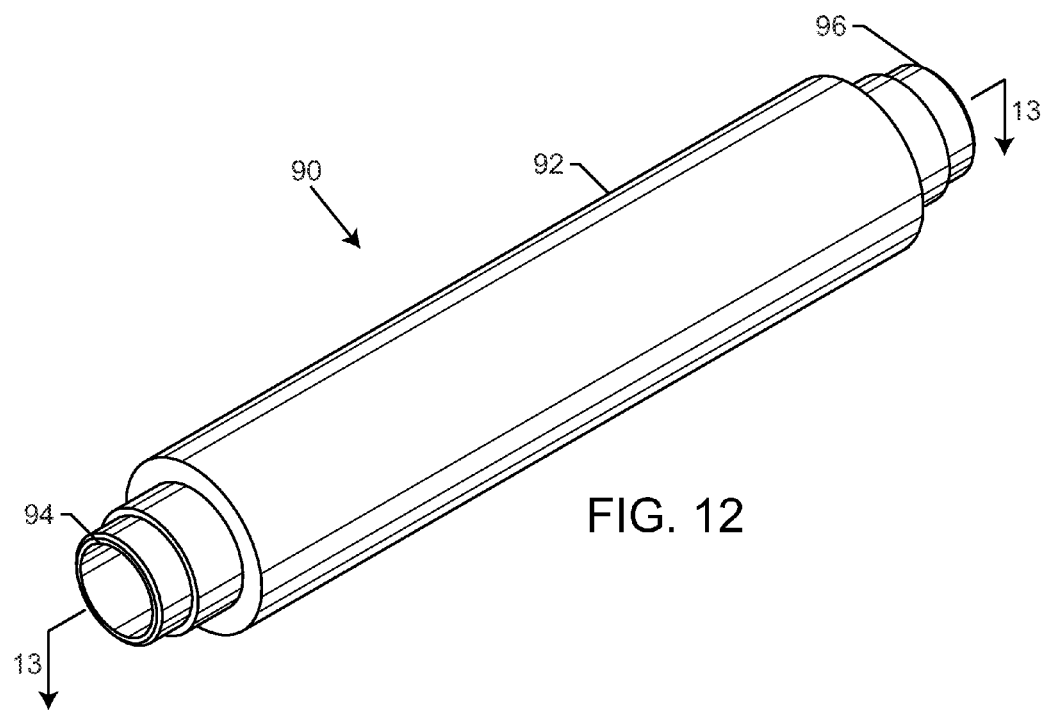
FIG. 12 is a perspective view another preferred embodiment of a multi-stage cavitation device.
Figure 13:
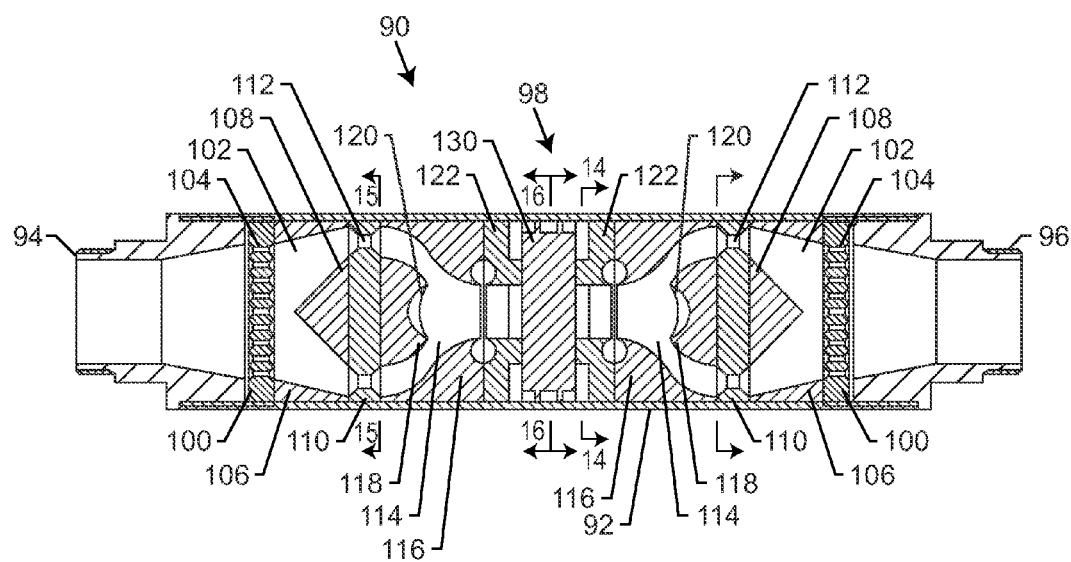
FIG. 13 is a cross-sectional view taken along line 13-13 of FIG. 12.

Another alternate embodiment for a flow-through cavitation device 90, as depicted in FIGS. 12 and 13, is comprised of a steel housing 92, which is attached to inlet 94 and outlet 96 pipes for direct connection to an industrial pipeline (not shown). The device 90 preferably has a mirrored symmetry such that from the inlet 94 to a mid-point 98 is repeated in reverse from the mid-point 98 to an outlet 96. The following description will follow the mirrored symmetry and describe from both the inlet 94 and outlet 96 toward the mid-point 98 simultaneously.

Assuming flow from left to right, front and end disk multi-jet nozzles 100 serve as the front and back walls of exterior working chambers 102 and are located behind the inlet pipe 94 and in front of the outlet pipe 96. The multi-jet nozzles 100 are equipped with constricting and expanding channels 104 that are distributed uniformly over the surfaces of the disks that are the multi-jet nozzles 100. The working chambers 104 are comprised of radial cones 106 and central guide cones 108, which are attached to radial multi-jet nozzles 110. The radial multi-jet nozzles 110 feature both constricting and expanding channels 112. The channels 112 are spread evenly over the radial perimeter surface of the nozzles 110, which direct the flow to interior working chambers 114.

Flow guides 116 that direct the flowpath from the perimeter to a center of the device 90 bound the chambers 114.

The cross-section of the flow guides 116 generally has an S-shape configuration. A hemi-spherical body 118 with a top niche 120 is mounted in the working chambers 114 against the multi-jet nozzle 110. The turbulizer disk 122 (FIG. 14) with curved guides 124 and central hole 126 is located behind the guides 124 in vortex chamber 128. The vortex chamber 128 is formed of the inner wall of the housing 92 and a cylindrical body 130 disposed in the center. The vortex chamber 128 directs the flow from the hole 126 of the front disk 122, around the cylindrical body 130 and out the hole 126 in the rear disk 122. The holes 126 in the front and rear disks 122 are coaxial. Their diameters are equal to that of holes in the guides 116. The mid-point 98 is within the vortex chamber 128.

Figure 17:
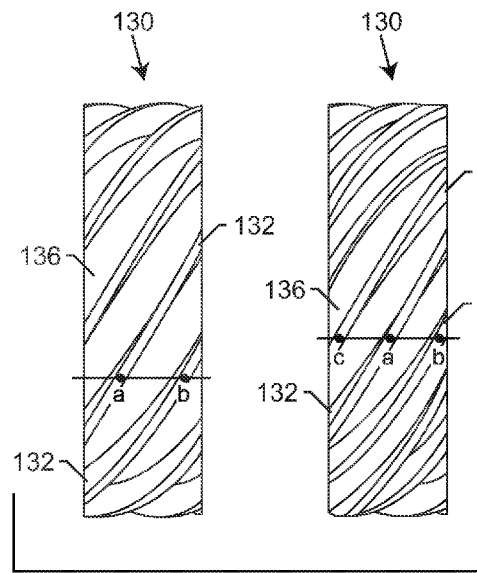
FIG. 17 is a side view of the cylindrical body.
Figure 18:
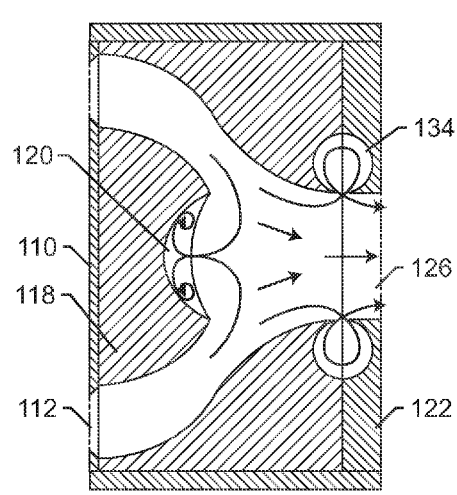
FIG. 18 is a close-up view of the front interior working chamber and toroidal vortex chamber illustrating fluid flow.
Figure 19:
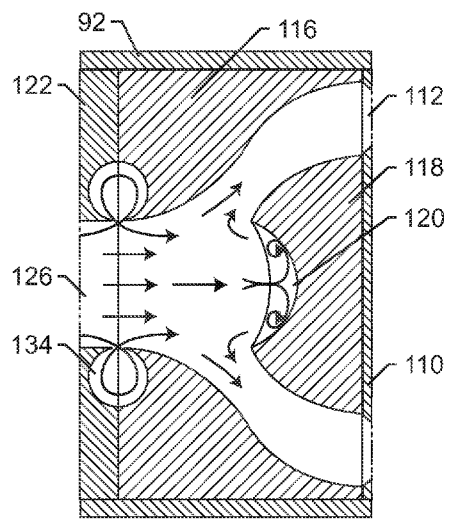
FIG. 19 is a close-up view of the back interior working chamber and toroidal vortex chamber illustrating fluid flow.
Figure 20:
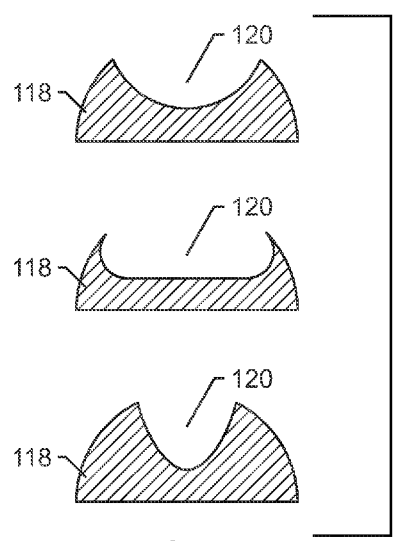
FIG. 20 is a cross-sectional view of various forms of the hemi-spherical body.

FIG. 14 is a diagram that shows disks 122 with curved guides 124 and central holes 126. An interior side of the radial multi-jet nozzles 110 is depicted in FIG. 15. The channels 112 let out into the working chambers 114 housing the hemi-spherical body 118 with the top niche 120. FIG. 16 shows a cross-sectional view of the cylindrical body 130, which is provided with the superficial perimeter guides 132 that serve as the channels for fluid flow. FIG. 17 is a drawing of a preferred embodiment for the guides 132 of the cylindrical body 130. FIGS. 18 and 19 depict the junction between the working chambers 114 and the disks 122 and illustrate fluid flow. At the junction between the guides 124 and the disks 122 are toroidal vortex chambers 134 which are connected to the holes 126 and working chambers 114. FIG. 20 is a simplified schematic illustration showing various embodiments for the niche 120: a hemi-sphere, a toroid, and a parabola.

The flow-through cavitation device 90 operates as follows. Fluid, for example, a rough disperse emulsion, is pumped in the inlet pipe 94. The fluid moves to the multi-jet nozzle 100 and passes through its channels 104, which have both constrictions and expansions. Flowing through the channels 104 causes the formation of vortices, detached flows and cavitation. Particles of the emulsion become subjected to shear forces, and emulsion quality improves. When cavitation bubbles reach the working chamber 102 they pulsate and collapse. The bubble implosion results in increased pressure and temperature and formation of local jets that act on the emulsion particles, further improving the emulsion homogeny. Then the flow moves in a converging cone formed by the radial cone 106 and the central cone 108 that is mounted on the radial multi-jet nozzle 110. The flow is accelerated as it passes through the converging cone and then enters the channels 112, which possess both constrictions and expansions to generate vortices, detached flows and cavitation in the fluid flow.

After passing through the radial multi-jet nozzle 110, the flow moves into the interior working chamber 114 where the cavitation bubbles pulsate and implode. When fluid flow moves down along the surface of the hemi-spherical body 118 it falls off the sharp edges of the top niche 120 generating toroidal vortices and a cavitation zone within the end of the working chamber 114. This cavitation field is characterized by a high intensity and a large cavity concentration. The end of the flow guide 116 is shaped as a constricting nozzle. The hole 126 in the disk 122 is shaped as an expanding nozzle in the beginning and a toroidal resonator 134 is positioned in the constrict location.

When the fluid flows along the place of the attachment of the flow guide 116 to the disk 122 it enters the ring grooves or toroidal resonator 134. The working principle of the toroidal resonator 134 is based on a high sensitivity of an symmetric flow to a side pressure. Changing pressure at the jet origination point will result in angular alteration of the fluid flow. The fluid is forced off the toroidal resonator 134 by discrete portions, which generates dynamic pulsations, vortices and cavitation. The frequency of a toroidal resonator depends on its diameter (Agranat et al., 1987).

The flow moves out of the working chamber 114, accelerating due to passing through the hole 126 in the front disk 122 and then enters channels located between the guides 124 on the front disk 122 in the vortex chamber 128. To maintain the fluid flow in a vortex state and to prevent it from moving in a plane parallel to the cavitator central axis, the guides 132 are provided on the cylinder 130 surface to direct the flow into channels 136 and sustain the spiral flow state. In the vortex chamber 128, cavitation bubbles are acted upon by centrifugal and Coriolis forces. As a result, the fluidic pressure rises and the bubbles collapse.

The direction of the flow moving down the channels 136 formed by the guides 132 provided on the cylinder 130 surface is determined by the pitch angle with respect to the central axis of the cavitation device 90. In order to prevent flow from following the straight path, certain requirements must be met. Lines that are parallel to the main axis and go through any point on the surface of a guide 132 should intersect the adjacent guide 132. In FIG. 17, a straight line parallel to the central axis, goes through point a on the guide 132 and intersects the adjacent guide 132 at point b. The more guides that are intersected by a straight line (points c, a and b), the better the flow is twirled in the vortex chamber 128. The number of guides 132 that may be intersected by one line is limited due to the requirement that the total area of the guide channels 136 be equal to the area of the central hole 126 of the disks 122. The total cross-sectional area of the channels 136 can be calculated by multiplying the number of channels by the height and width.

After passing through the channels 136 the fluid flow moves over the surface of the vortex guides 124 and enters the hole 126 in the rear disk 122. This directs the flow along the central axis of the device 90. When the fluid flow passes the rear disk 122 and rear guide 116 it enters the rear toroidal resonator 134, the working principle of which is described above. The accelerated flow falls on the top niche 120 of the rear hemi-spherical body 118, forming a pulsating toroidal vortex and cavitation zone (Dudzinskii and Nazarenko, 1996; Nazarenko, 1998). The pulsation frequency and the cavitation zone shape depend on the fluid properties, flow rate and the niche shape. The preferred embodiments for the niche 120 are described above.

The fluidic flow passes through the region of the toroidal resonator 134 and niche 120 and enters the working chamber 114 bounded by the rear guide 116 inner wall and the rear semi-spherical body 118, which together direct the flow from the central axis to the perimeter of the device 90. The cavities detached from the toroidal flow region implode in the working chamber 114. After passing the working chamber 114, the fluid flow enters channels 112 of the rear radial multi-jet nozzle 110 provided with the constrictions and the expansions. This generates vortices, detached flow jets and cavitation. When the fluid flow moves in the working chamber 102, the flow velocity decreases, the pressure goes up, and pulsation and implosion of the bubbles take place. Then the flow passes through the constrictions and the expansions in the channels 104 of the rear disk multi-jet nozzle 100 followed by generation of vortices, detached flow jets and cavitation. The particles of emulsion that undergo the cavitation process are reduced in size and their surfaces are modified. The cavitation bubbles pulse and implode within the working chamber 102, leading to shear force and local jet formation. Then the fluid flow exits the cavitation device through the outlet 96.

This preferred embodiment of the device provides at least eleven cavitation zones: (1) the front multi-jet nozzle 100; (2) the front, radial multi-jet nozzle 110; (3) the top niche 120 in the front hemi-spherical body 118; (4) the front toroidal vortex chamber 134; (5) the hole 126 and curved guides 124 of the front disk 122; (6) the vortex chamber 128; (7) the hole 126 and curved guides 124 of the rear disk 122; (8) the rear toroidal vortex chamber 134; (9) the top niche 120 in the rear hemi-spherical body 118; (10) the rear, radial multi-jet nozzle 110; and (11) the rear-end multi-jet nozzle 100. The device design allows for two, four, six or even more mirror-symmetric cavitation regions. The plane of mirror symmetry goes through the mid-point 98 of the vortex chamber 128 located between the disks 122.

One of the numerous advantages of this embodiment is its versatility in respect to fluid feeding. The device 90 can be connected to a pump at either end and is especially suitable for technological applications with a demand for reversing flow direction. The device 90 can be incorporated in a pipeline without any risk of confusing inlet with outlet. The main benefit of the present flow-through cavitation device 90 is the interface of the vortex and cavitation generating zones with the higher-pressure working chambers for the implosion of cavitation bubbles.

Figure 21:
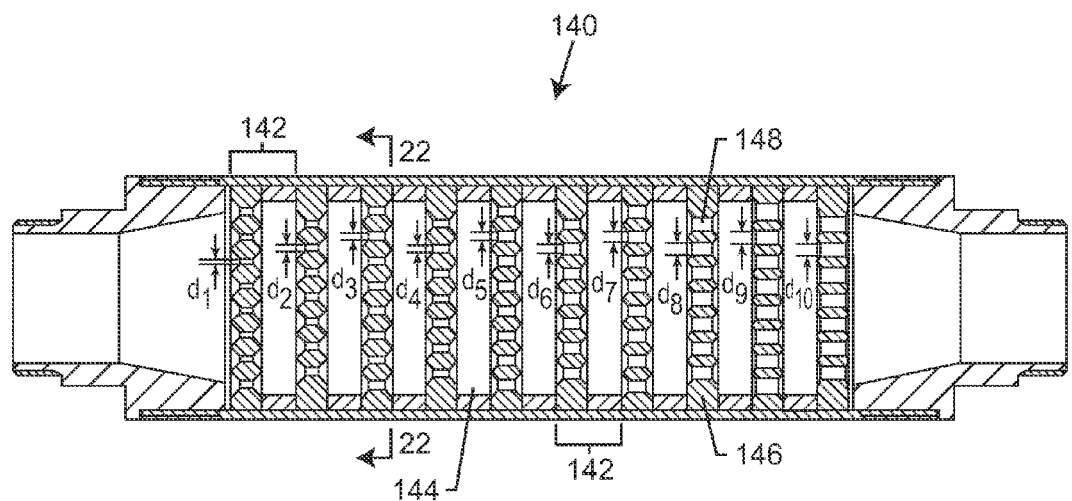
FIG. 21 is a cross-sectional view of another preferred embodiment of the multi-stage flow-through hydrodynamic cavitation device.
Figure 22:
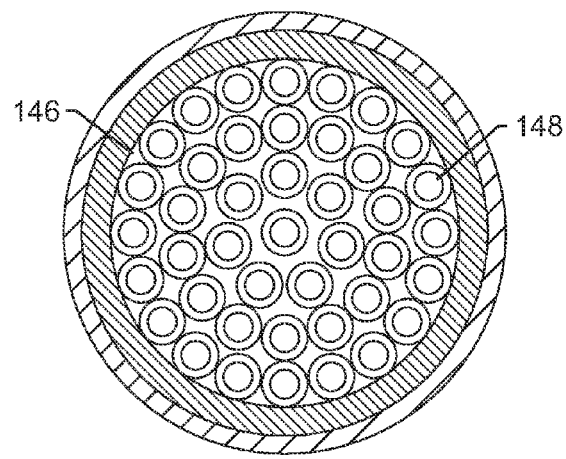
FIG. 22 is a cross-sectional view taken along line 22-22 of FIG. 21.

FIGS. 21 and 22 illustrate another alternate embodiment for a flow-through multi-stage cavitation device 140 that provides as many as ten zones 142 for generation and collapse of cavitation bubbles and is comprised of ten identical working chambers 144 and ten multi-jet nozzles 146 that differ in respect to the cross-sectional passage areas created by their channels 148. When fluid is fed in the cavitation device 140 through a displacement pump or other means, the flow rate is the same within the identical, sequentially located multi-jet nozzle channels 148. Thus, it is possible to lower the fluid flow rate within the channels of nearby downstream multi-jet nozzles, while keeping the cavitation at the same level. When the fluid flow passes through the front multi-jet nozzle 146 and the working chamber 144, the cavities implode and the fluid's temperature rises. The increased temperature and amplification of the nuclei facilitate the onset of cavitation events in downstream cavitation zones 142. Therefore, the same cavitation number and the same cavitation bubble concentration can be achieved within downstream zones with the lower flow velocity inside the nozzle channels 148.

During multi-stage fluid processing the hydraulic resistance is reduced by meeting the following condition: The cross-sectional channel area ($S_n$) of each multi-jet nozzle 146 is less than the cross-section channel area ($S_{n+1}$) of the next multi-jet nozzle 146 along the flowpath, according to the equation:

$$1.0 \leq S_{n+1} S_n \leq 1.1,$$

where n=1, 2, 3, 4, 5, 6, 7, 8 or 9. This save energy required for pumping a fluid flow through the multi-zone cavitation device 140. To scale back the cavitation device parts, for example, the multi-jet nozzle 146, it is necessary to place the channels 148 for fluid passage as close as possible. The number of the channels 148 of the multi-jet nozzle 146 is limited by the ratio of the total area of the largest cross-sectional openings ($S_d$) of the channels 148 to the surface area ($S_D$) of the multi-jet nozzle 146, such that $S_d/S_D \leq 0.8$, where $$S_d = \sum_{i=1}^{k} S_i$$

(k is the number of channels of the multi-jet nozzle; $S_i = \pi d_i^2/4$, where $d_i$ is the largest diameter of the channels I, and $S_D = \pi D^2/4$, where D is the multi-jet nozzle diameter.

The present invention employs a specific process for extracting carbohydrates from biomass and creating bioalcohol using hydrodynamic cavitation in fluids. The process involves flowing a fluidic mixture through the cavitation device having a specified inlet flow velocity and system pressure through acceptable piping and pumping means. The inlet velocity and system pressure vary according to the reaction mixture properties. The preferred flow rate is approximately ten gallons per minute, but may be adjusted lower or higher according to output requirements without affecting the results of the cavitation process. The preferred system pressure is 25-5,000 psi. In a particularly preferred embodiment, the inlet velocity is ten gallons per minute and the system pressure is about 500 psi.

The apparatuses and methods described herein, subject to the conditions and specifications of usage, provide a method for extracting carbohydrates from biomass and producing bioalcohol. The processing is dependant upon the properties of the fluidic reaction mixture being processed and the energy requirements necessary to generate cavitation in the fluid.

The inventive method and cavitation device may be used in any combination of single-pass, multi-pass, parallel flow, series flow, or other variations of deployment to render the desired result. As this invention applies to the chemical and physical nature of the process occurring within the cavitation device, it also covers any array of deployment or fluid circuitry allowable by such device.

Thus, the disclosed method represents an advanced and highly optimized approach that allows completing extraction and conversion by applying a flow-through passage of the fluid medium through the hydrodynamic cavitation device. Apart from known methods, the proposed method's efficiency is not a function of the degree of mixing but rather a function of the unique gas-solid/liquid interaction conditions allowing the high conversion rates and minimal residency time. The proposed process is based on the formation of short-lived gas bubbles comprised of volatile components, their subsequent growth, pulsation, and controlled implosions within the solid/liquid phase. The cavitation is the cornerstone of the present process, which consists of generating cavitation by introducing the reaction mixture to a flow-through cavitation device provided with the sequential compartments of varying diameters and inner surface features, reducing the pressure of fluidic medium (reaction mixtures) such that it approaches the gas/liquid threshold of the volatile components, and conducting the cavitation such that there is the generation of vapor bubbles followed by their implosion in high-pressure zones.

The present process significantly differs from all other known methods by supplying the unique, previously unknown reaction conditions for conducting the advanced gas-solid/liquid extraction processes. The method allows for shorter reaction times and higher yields by creating optimal conditions required for the gas-solid/liquid processes to proceed to their completion. Since the transient gas phase is represented by the enormous number of short-lived alcohol vapor-filled micro bubbles distributed throughout the fluidic reaction mixture, the proposed method provides a very large interphase reaction surface, superior mixing and the prompt separation of reaction mixture. The hydrodynamic cavitation-assisted gas-solid/liquid processing is characterized with improved efficiency in comparison with other methods.

The proposed cavitation devices are particularly efficient at mixing the biomass with reagents and generating in this mixture the transient cavitation features followed by separation of the reaction mixture comprised of the extracted carbohydrates, residual initial reagents, remaining biomass, and other by-products. The flow-through hydrodynamic cavitation-assisted extraction processes can be carried out in-line rather than using time-consuming batch processing. An industrial scale device may allow large scale processing each day.

Figure 23:
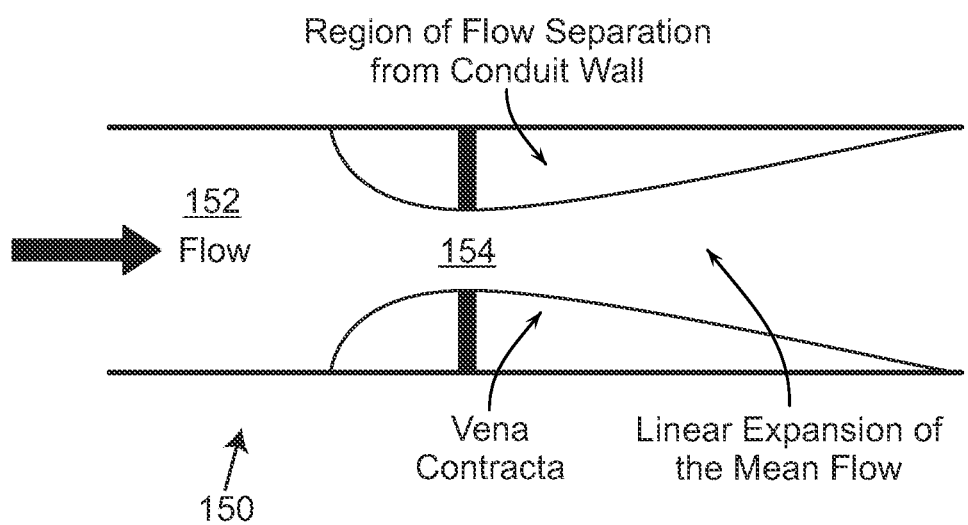
FIG. 23 is a cross-sectional view of a flow orifice used in numerical simulations of hydrodynamics cavitation processes.
Figure 24A:
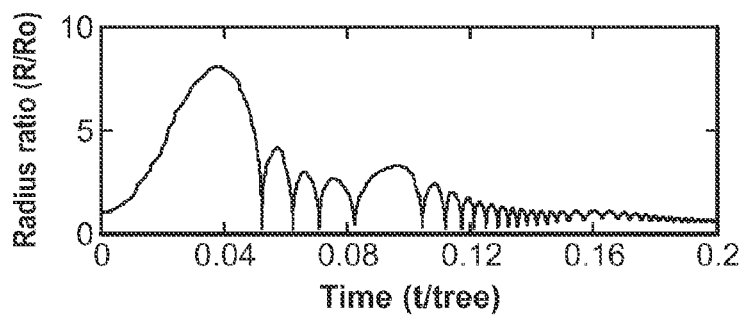
FIG. 24A is a graph illustrating Radius Ratio versus Time of a first permutation of a numerical simulation of the cavitation process.
Figure 24B:
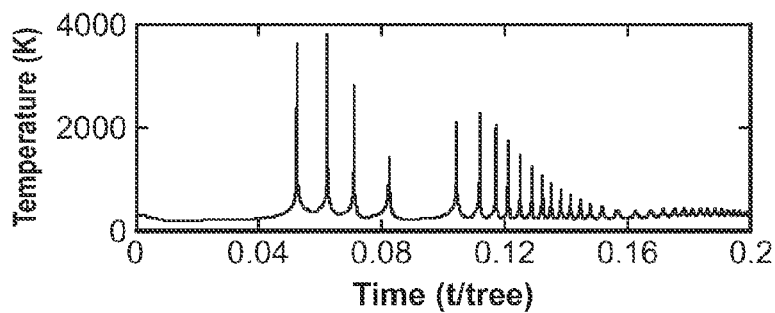
FIG. 24B is a graph illustrating Temperature versus Time of a first permutation of a numerical simulation of the cavitation process.
Figure 24C:
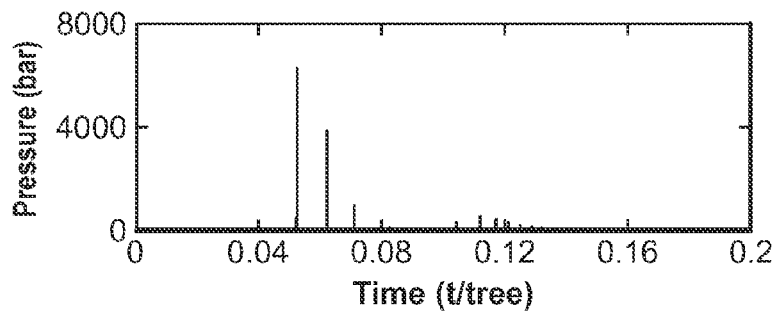
FIG. 24C is a graph illustrating Pressure versus Time of a first permutation of a numerical simulation of the cavitation process.
Figure 24D:
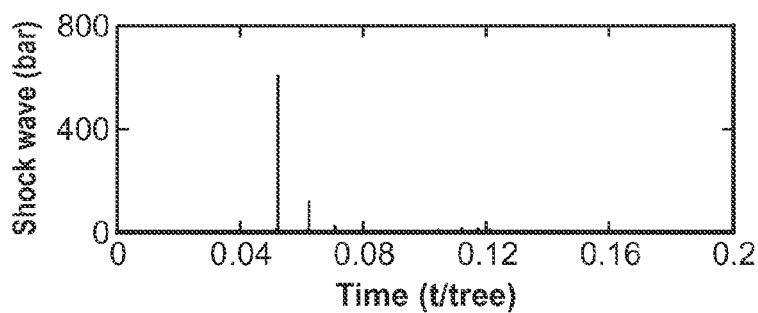
FIG. 24D is a graph illustrating Shockwave versus Time of a first permutation of a numerical simulation of the cavitation process.
Figure 24E:
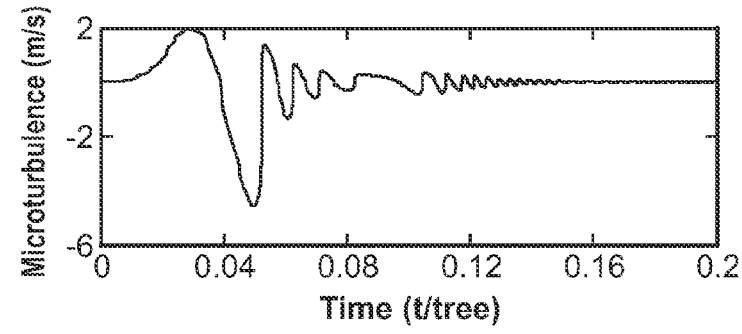
FIG. 24E is a graph illustrating Microturbulence versus Time of a first permutation of a numerical simulation of the cavitation process.
Figure 25A:
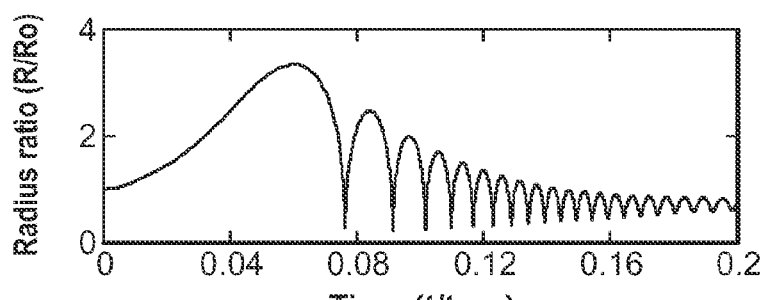
FIG. 25A is a graph illustrating Radius Ratio versus Time of a second permutation of a numerical simulation of the cavitation process.
Figure 25B:
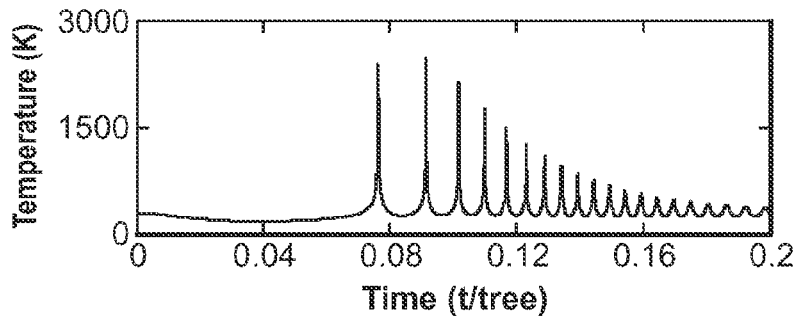
FIG. 25B is a graph illustrating Temperature versus Time of a second permutation of a numerical simulation of the cavitation process.
Figure 25C:
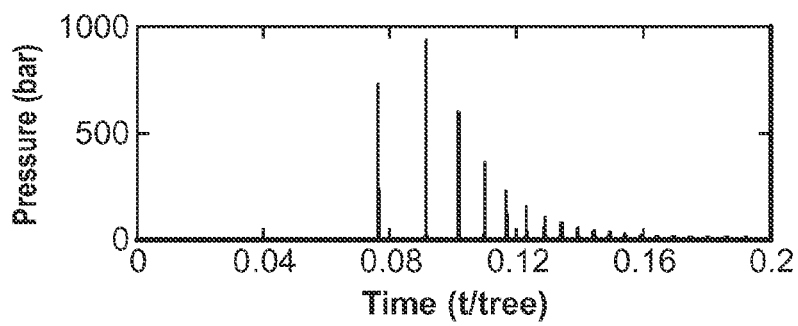
FIG. 25C is a graph illustrating Pressure versus Time of a second permutation of a numerical simulation of the cavitation process.
Figure 25D:
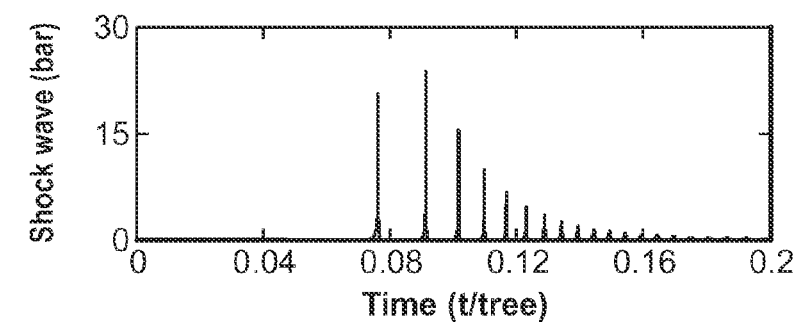
FIG. 25D is a graph illustrating Shockwave versus Time of a second permutation of a numerical simulation of the cavitation process.
Figure 25E:
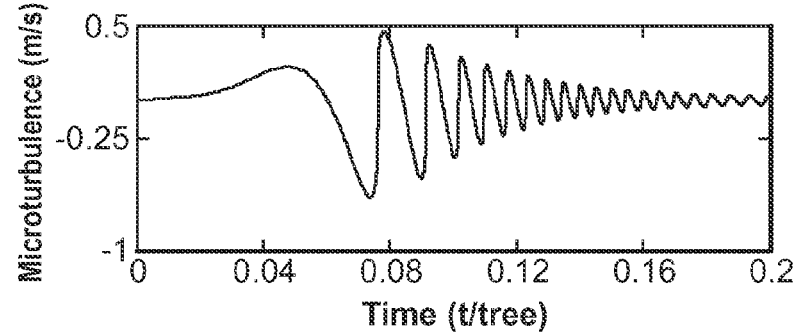
FIG. 25E is a graph illustrating Microturbulence versus Time of a second permutation of a numerical simulation of the cavitation process.
Figure 26A:
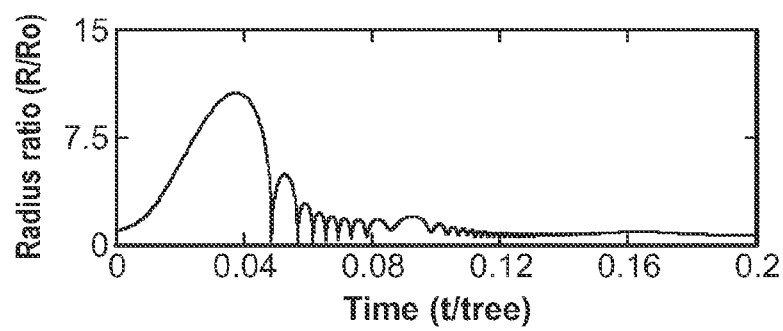
FIG. 26A is a graph illustrating Radius Ratio versus Time of a third permutation of a numerical simulation of the cavitation process.
Figure 26B:
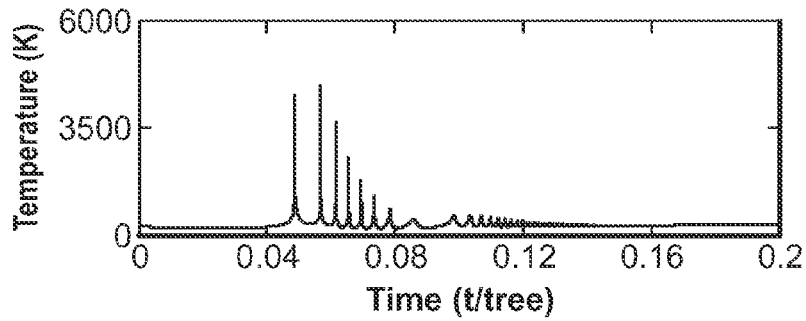
FIG. 26B is a graph illustrating Temperature versus Time of a third permutation of a numerical simulation of the cavitation process.
Figure 26C:
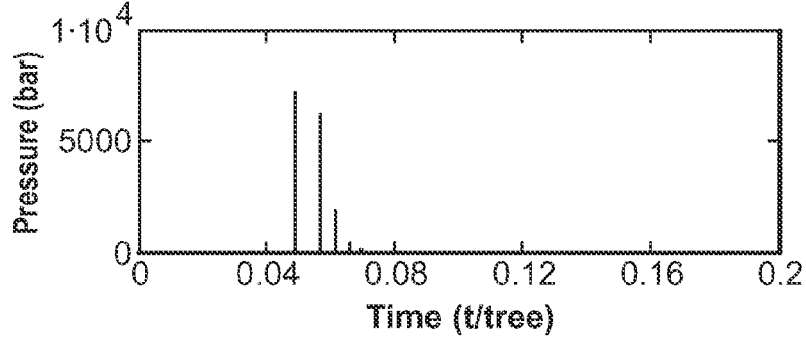
FIG. 26C is a graph illustrating Pressure versus Time of a third permutation of a numerical simulation of the cavitation process.
Figure 26D:
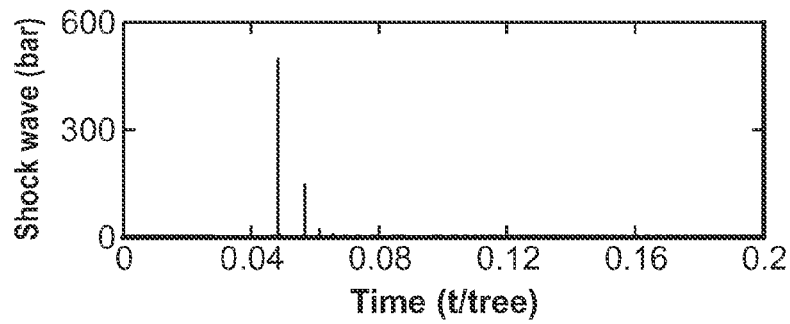
FIG. 26D is a graph illustrating Shockwave versus Time of a third permutation of a numerical simulation of the cavitation process.
Figure 26E:
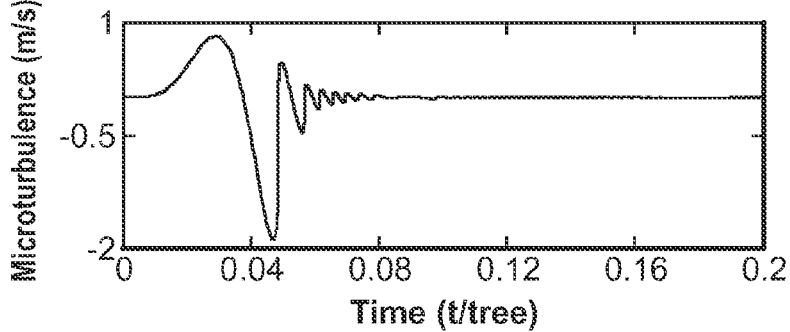
FIG. 26E is a graph illustrating Microturbulence versus Time of a third permutation of a numerical simulation of the cavitation process.
Figure 27A:
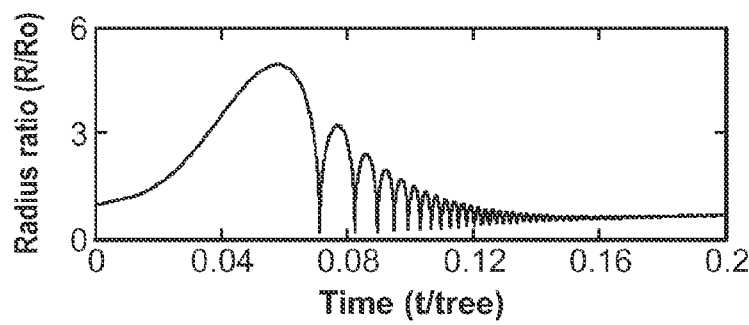
FIG. 27A is a graph illustrating Radius Ratio versus Time of a fourth permutation of a numerical simulation of the cavitation process.
Figure 27B:
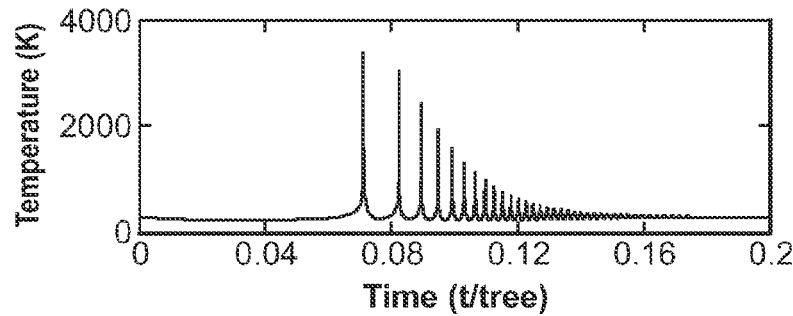
FIG. 27B is a graph illustrating Temperature versus Time of a fourth permutation of a numerical simulation of the cavitation process.
Figure 27C:
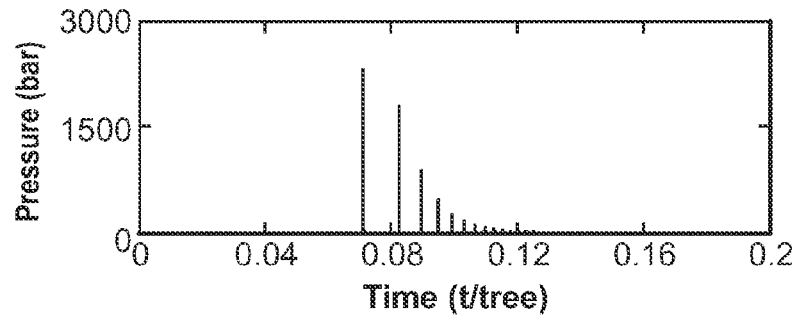
FIG. 27C is a graph illustrating Pressure versus Time of a fourth permutation of a numerical simulation of the cavitation process.
Figure 27D:
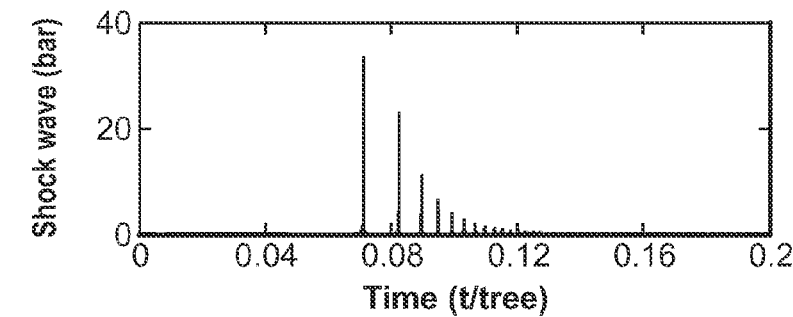
FIG. 27D is a graph illustrating Shockwave versus Time of a fourth permutation of a numerical simulation of the cavitation process.
Figure 27E:
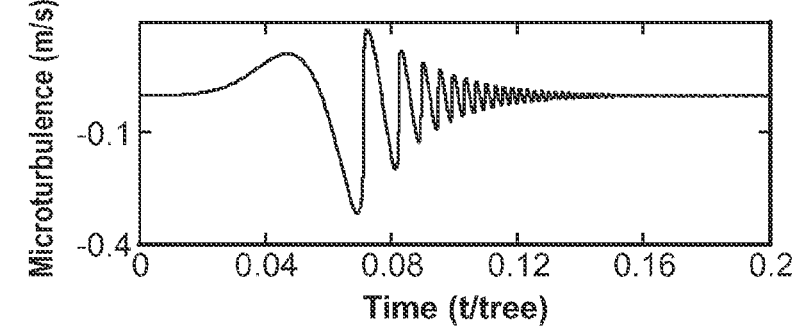
FIG. 27E is a graph illustrating Microturbulence versus Time of a fourth permutation of a numerical simulation of the cavitation process.

Numerical simulations of the cavitation described herein have been performed based upon a flow geometry having an orifice section 150 similar to that depicted in FIG. 23. The inlet section 152 of the orifice has a diameter approximately twice that of the throat section 154. The flow geometry of a nozzle or other constriction preferably has a similar ratio of dimensions. The simulations were performed for an air bubble with incorporation of the turbulent fluctuations. The estimation of turbulent fluctuation velocity was performed using Kolmogoroff's hypothesis that the rate at which large eddies supply energy to the smaller eddies is proportional to the reciprocal of the time scale of larger eddies.

The gas bubbles may already be present in the liquid medium (i.e. water) or they may be small gas pockets trapped in the crevices in the wall of the conduit (or solid boundaries of the flow). As noted earlier, the gas bubble may also form in the flow due to release of the dissolved gas at or immediately downstream of the vena contracta, where the velocity increase and the pressure decrease are at their extremes. If the bulk pressure of the flow at the throat of the constriction falls close to or even below the vapor pressure of the solvent, localized evaporation of liquid solvent is likely to occur resulting in formation of vapor bubbles. However, the vapor inside these bubble condenses rapidly with the recovery of bulk pressure in the downstream region, and hence, the bubbles do not contribute much to the transient cavitation.

On a relative basis, the contribution of gas bubbles is higher than the vapor bubbles in the transient cavitation. One major assumption in the simulations is that the bubbles are always at mechanical equilibrium with the surrounding liquid. This means that the pressure inside the bubble is assumed to be equal to the bulk pressure in the surrounding liquid plus the Laplace pressure ($2\sigma/R_o$), where $\sigma$ is the surface tension of the liquid.

The numerical simulations essentially give a time history of several parameters: bubble radius (R); velocity of the bubble wall (i.e. the time derivative of the bubble radius); temperature inside the bubble; pressure inside the bubble; micro-turbulence generated by the bubble; and shock waves (or acoustic waves) generated by the bubble. Temperature and pressure inside the bubble are representative of the sonochemical effect, while micro-turbulence and shock wave generated by the bubble are representative of the sonophysical effect. In the present context of biomass pretreatment, the micro-turbulence and shock waves are of relevance.

The simulations were performed using permutation—combination of a few main parameters, namely: initial bubble radius, $R_o$; ratio of orifice to throat diameters, $\beta$; and the cavitation number at the vena contracta, $C_i$. Two representative values for each of these parameters were chosen, which are very similar to the actual values of these parameters in the inventive hydrodynamic cavitation device. These values are: $R_o$=50 and 100 microns; $\beta$=0.5 and 0.7; and $C_i$=0.8 and 1.0. Permutation—combinations of these parameters can result in up to 8 sets of values for simulations. Four sets were selected for simulations, the results of which are shown graphically in FIGS. 24-27.

FIGS. 24A-24E present simulation data for $R_o$=100 microns, $\beta$=0.5, and $C_i$=1.0—with a pump pressure of 35 bar (or approximately 500 psi) and a recovery pressure of 8.5 bar. FIGS. 25A-25E present simulation data for $R_o$=100 microns, $\beta$=0.7, and $C_i$=0.8—with a pump pressure of 35 bar (or approximately 500 psi) and a recovery pressure of 17.5 bar. FIGS. 26A-26E present simulation data for $R_o$=50 microns, $\beta$=0.5, and $C_i$=1.0—with a pump pressure of 35 bar (or approximately 500 psi) and a recovery pressure of 8.5 bar. FIGS. 27A-27E present simulation data for $R_o$=50 microns, $\beta$=0.7, and $C_i$=0.8—with a pump pressure of 35 bar (or approximately 500 psi) and a recovery pressure of 8.5 bar. The simulation data presented in each of these graphs report radius ratio, temperature, pressure, shock wave, and microturbulence values over time resulting from the simulated cavitation process.

The graphs of FIGS. 24A-27E show the generation of intense micro-convection due to cavitation bubbles. This micro-convection has contribution from high intensity shock waves—with pressure amplitude in the range of 40 to 600 bar—and also strong microturbulence with oscillatory velocities in the range of 0.4 to 6 m/s. It is noteworthy that this extreme micro-convection is generated on an extremely small spatial scale and is effective only in the close vicinity (~1 mm) of the surface of the bubble. Such convection is capable of generating strong micro-currents of bulk liquid in the biomass matrix that help with the removal of dissolved sugar and carbohydrate oligomers formed due to hydrolysis. Constant refreshing of the water in the biomass matrix enhances the rate of hydrolysis due to the fresh supply of hydrolyzing ions inside the biomass matrix and also dissolution of sugar and carbohydrate molecules leading to enhanced yield. The shock waves generated by microbubbles also help in expanding or swelling of biomass that increases the net voidage of the matrix allowing for smoother flow of liquid medium or water through the matrix.

For the use of the inventive hydrodynamic cavitation device in bioalcohol synthesis, these shock waves are highly instrumental in the disruption of the boundary between the phases. Shock waves essentially create a fine emulsion of the two phases with an enormous surface area (that is not achievable in any mechanically agitated device). This high interfacial area provides increased mass transfer across the phases. Thus, transient cavitation also helps in enhancing the kinetics of carbohydrate extraction as well as the yield.

For two combinations of parameters, namely, $\beta$=0.5 and $C_i$=0.8, both for 50 and 100 micron bubbles, the flow was observed to flash at the vena contracta. This essentially means that due to a low cavitation number the bulk pressure at the vena contracta falls below the vapor pressure of the liquid. In addition, the turbulent pressure fluctuations superimposed over it take the pressure further down and caused rapid evaporation of the liquid in the bulk flow. The liquid phase thus did not remain the continuous phase anymore, but became a dispersed phase in the vapor of the solvent. The simulations model ceased at these conditions.

For another set of parameters, namely, $\beta$=0.7, $C_i$=1.0 for both 50 and 100 micron bubbles, the turbulent pressure fluctuations were too weak to cause any remarkable growth of the cavitation bubbles that would result in transient ensuing collapse. These set of conditions did not generate a transient cavitation effect sufficient to enhance or intensify the process.

Although several embodiments have been described in some detail for purposes of illustration, various modifications may be made without departing from the scope and spirit of the invention. Accordingly, the invention is not to be limited, except as by the appended claims.

What is claimed is:

1. A process for creating bioalcohol from carbohydrates extracted from biomass comprising the steps of:
preparing the biomass for a first extraction of carbohydrates;
forming a first biomass solution comprising the prepared biomass, water, and an acid or an alkali;
subjecting the first biomass solution to a first hydrodynamic cavitation treatment, wherein acid or alkali hydrolysis of the biomass occurs;
filtering the first biomass solution into a first filtrate and an intermediate biomass, wherein the first filtrate contains extracted carbohydrates;
washing the intermediate biomass with water to remove the added acid or alkali and to prepare the intermediate biomass for a second extraction of carbohydrates;
creating a second biomass solution comprising the washed intermediate biomass, water and an enzyme source;
exposing the second biomass solution to a second hydrodynamic cavitation treatment, wherein enzymatic hydrolysis of the biomass occurs;
filtering the second biomass solution into a second filtrate and a filtered biomass, wherein the second filtrate contains extracted carbohydrates;
combining the first filtrate with a bacterial species and nutrients to form a first fermentation substrate;
fermenting the first fermentation substrate to form a first bioalcohol; and
separating the first bioalcohol from the first fermentation substrate using distillation, liquid-liquid extraction, or gas sparging.

2. The process of claim 1, wherein the bacterial species comprises *Escherichia Coli, Saccharomyces cerevisiae, Zymomonas mobilis, Lactobacillus buchneri,* or *Clostridium acetobutylicum.*

3. A process for creating bioalcohol from carbohydrates extracted from biomass comprising the steps of:
preparing the biomass for a first extraction of carbohydrates;
forming a first biomass solution comprising the prepared biomass, water, and an acid or an alkali;
subjecting the first biomass solution to a first hydrodynamic cavitation treatment, wherein acid or alkali hydrolysis of the biomass occurs;
filtering the first biomass solution into a first filtrate and an intermediate biomass, wherein the first filtrate contains extracted carbohydrates;
washing the intermediate biomass with water to remove the added acid or alkali and to prepare the intermediate biomass for a second extraction of carbohydrates;
creating a second biomass solution comprising the washed intermediate biomass, water and an enzyme source;
exposing the second biomass solution to a second hydrodynamic cavitation treatment, wherein enzymatic hydrolysis of the biomass occurs;
filtering the second biomass solution into a second filtrate and a filtered biomass, wherein the second filtrate contains extracted carbohydrates;
combining the second filtrate with a bacterial species and nutrients to form a second fermentation substrate;
fermenting the second fermentation substrate to form a second bioalcohol; and
separating the second bioalcohol from the second fermentation substrate using distillation, liquid-liquid extraction, or gas sparging.

4. The process of claim 3, wherein the bacterial species comprises *Escherichia Coli, Saccharomyces cerevisiae, Zymomonas mobilis, Lactobacillus buchneri,* or *Clostridium acetobutylicum.*

5. A process for creating bioalcohol from carbohydrates extracted from biomass comprising the steps of:
preparing the biomass for a first extraction of carbohydrates;
forming a first biomass solution comprising the prepared biomass, water, and an acid or an alkali;
subjecting the first biomass solution to a first hydrodynamic cavitation treatment, wherein acid or alkali hydrolysis of the biomass occurs;
filtering the first biomass solution into a first filtrate and an intermediate biomass, wherein the first filtrate contains extracted carbohydrates;
washing the intermediate biomass with water to remove the added acid or alkali and to prepare the intermediate biomass for a second extraction of carbohydrates;
creating a second biomass solution comprising the washed intermediate biomass, water and an enzyme source;
exposing the second biomass solution to a second hydrodynamic cavitation treatment, wherein enzymatic hydrolysis of the biomass occurs;
filtering the second biomass solution into a second filtrate and a filtered biomass, wherein the second filtrate contains extracted carbohydrates;
mixing the first filtrate with the second filtrate to form a blended filtrate;
combining the blended filtrate with a bacterial species and nutrients to form a blended fermentation substrate;
fermenting the blended fermentation substrate to form a blended bioalcohol; and
separating the blended bioalcohol from the blended fermentation substrate using distillation, liquid-liquid extraction, or gas sparging.

6. The process of claim 5, wherein the bacterial species are genetically modified and comprise *Escherichia Coli, Saccharomyces cerevisiae, Zymomonas mobilis, Lactobacillus buchneri,* or *Clostridium acetobutylicum.*

* * * * *